(12) United States Patent
Dias et al.

(10) Patent No.: US 6,623,936 B1
(45) Date of Patent: Sep. 23, 2003

(54) COMPOSITIONS AND METHODS FOR IMPROVED DETECTION AND CLASSIFICATION OF NEOPLASMS

(75) Inventors: Peter Dias, San Diego, CA (US); Sujay Singh, San Diego, CA (US)

(73) Assignee: Imgenex, San Diego, CA (US)

( * ) Notice: Subject to any disclaimer, the term of this patent is extended or adjusted under 35 U.S.C. 154(b) by 0 days.

(21) Appl. No.: 09/499,559

(22) Filed: Feb. 7, 2000

Related U.S. Application Data

(60) Provisional application No. 60/155,972, filed on Sep. 24, 1999.

(51) Int. Cl.[7] .............................................. G01N 33/53
(52) U.S. Cl. .......................... 435/7.2; 435/6; 435/7.1; 435/7.9; 435/7.91; 435/7.93; 435/7.95; 530/350; 530/387.1
(58) Field of Search ..................... 435/6, 7.1, 7.23, 435/7.9, 7.91, 7.92, 7.93, 7.94, 7.95; 530/350, 387.1

(56) References Cited

U.S. PATENT DOCUMENTS

| | | | |
|---|---|---|---|
| 3,770,383 A | 11/1973 | Price | |
| 4,468,371 A | 8/1984 | Chen | |
| 4,591,570 A | 5/1986 | Chang | |
| 5,223,220 A | 6/1993 | Fan | |
| 5,244,788 A | 9/1993 | Hubscher | |
| 5,270,167 A | 12/1993 | Francoeur | |
| 5,340,739 A | * 8/1994 | Stevens et al. | 435/240.1 |
| 5,432,099 A | 7/1995 | Ekins | |
| 5,486,452 A | 1/1996 | Gordon | |
| 5,688,918 A | 11/1997 | Kulesz-Martin | |
| 5,763,198 A | 6/1998 | Hirth et al. | |
| 5,807,522 A | 9/1998 | Brown | |
| 5,824,770 A | 10/1998 | Georgopoulos | |
| 5,858,682 A | 1/1999 | Gruenwald | |
| 5,858,801 A | 1/1999 | Brizzolara | |
| 5,866,350 A | 2/1999 | Canavaggio | |
| 5,876,949 A | 3/1999 | Dreyfuss | |
| 5,885,769 A | 3/1999 | Kumar | |

OTHER PUBLICATIONS

1/ Bonche M et al. Exp. Cell Res. 208(1): 209–17, 1993.*
Wang, NP, 1996, Modern Pathol, 9(5): 496–506.*
Wang, NP et al, 1995, Amer J Pathol, 147(6): 1799–1810.*
Tonin, PN et al, 1991, Cancer Res, 51 (19): 5100–5106.*
Lewis et al, 1991, Cellular Immunol, 132(1): 158–67.*

Athanasious et al, Cell Growth Differ. 7:1525–1534 (1996).
Baringa et al., Oxf. Surv. Eurkaryot. Gene 2:49–73 (1985).
Bejarano et al., Mod. Pathol. 9:445–452 (1996).
Bolon et al., Lab. Invest. 75:1–13 (1996).
Buonanno et al., Nucleic Acids Res. 20:539–544 (1992).
Dale et al., Histopathology 14:493–502 (1989).
Dias et al., Cancer Res. 52:6431–6439 (1992).
Dias et al., Seminars in Diagnostic Pathology 11:3–14 (1994).
DiLoreto et al., J. Clin. Pathol. 50:30–32 (1997).
Folpe et al., Mod. Pathol. 12:5–8 (1999).
Green et al., British Journal of Dermatology 139:911–915 (1998).
Hida et al., Oral Oncol. 33:426–430 (1997).
Hirsch et al., Cancer 62:973–977 (1988).
Kishimoto et al., Cell Growth & Diff. 9:337–344 (1998).
Maitland et al., J. Path. 186:275–280 (1998).
Marcelino et al., BioTechniques 26:1134–1148 (1999).
McKay et al., Am. J. Respir. Cell Mol. Biol. 18:823–833 (1998).
Meyyappan et al., Biol. Signals 5:130–138 (1996).
Montarras et al., The New Biologist 3:592–600 (1991).
Okuzawa et al., Electrophoresis 15:382–390 (1994).
Parham et al., Acta Neuropathol. (Berl.) 87:605–611 (1994).
Postmus et al., Cancer 57:60–63 (1986).
Rosai et al., Am. J. Surg. Pathol. 15:974–981 (1991).
Sun et al., Proc. Natl. Acad. Sci. USA 96:680–685 (1999).
Swanson, Prog. Brain Res. 92:97–113 (1992).
Tallini et al., Am. J. Pathol. 144:693–701 (1994).
Tome et al., Acta Cytol. 35:485–490 (1991).
Turner et al., Cancer Res. 58:5466–5472 (1998).
Vandromme et al., Trends Biochem. Sci. 21:56–64 (1996).
Wesche et al., Am. J. Surg. Pathol. 19:261–269 (1995).

* cited by examiner

Primary Examiner—Susan Ungar
Assistant Examiner—Minh-Tam Davis
(74) Attorney, Agent, or Firm—David R. Preston & Associates; David Preston

(57) ABSTRACT

A method for diagnosing clinically distinct embryonal and alveolar subtypes of rhabdomyosarcoma, including contacting a reagent including an antibody that specifically binds myogenin with a sample that includes at least one rhabdomyosarcoma cell or at least one extract of at least one rhabdomyosarcoma cell, detecting the binding of the antibody to the sample to determine the presence, absence, or amount of myogenin in the sample, and diagnosing clinically distinct embryonal and alveolar subtypes of rhabdomyosarcoma, alveolar rhabdomyosarcoma having an increased amount of binding as compared to embryonal rhabdomyosarcoma.

5 Claims, 2 Drawing Sheets

US 6,623,936 B1

COMPOSITIONS AND METHODS FOR IMPROVED DETECTION AND CLASSIFICATION OF NEOPLASMS

PRIORITY INFORMATION

This application claims benefit of priority to U.S. Provisional Patent Application Ser. No. 60/155,972 to Dias et al., filed Sep. 24, 1999, which is incorporated herein by reference.

This invention was made with government support awarded by the National Institutes of Health, grant number 7R44 CA 60198. The United States Government has certain rights in the invention.

TECHNICAL FIELD

The present invention generally relates to compositions and methods for the improved detection and classification of neoplasms such as malignancies, preferably using specific binding reagents, such as antibodies.

BACKGROUND

The ability to accurately diagnose neoplasms, including the ability to differentiate between benign and malignant cells, is central to the successful treatment and subsequent survivability and quality of life of those fallen victim to cancer. The penalty for error in such diagnosis is high for the patient. For example, if a malignant growth is improperly diagnosed as benign, then the patient has poor prognosis compared to patients accurately diagnosed and correctly treated. Furthermore, if a benign growth is diagnosed as malignant, then the patent may be subjected to unnecessary and costly treatments that themselves can be life threatening. Current preferred methods of diagnosis of neoplasia rests on visual observation of samples of tissues, fluids or tumors taken from a patent. The samples can be prepared in a variety of ways, including histochemical staining with a variety of reagents, which assist a pathologist in determining, morphological, cellular and/or tissue structures and appearances upon observation with a microscope. However, such methods tend to be imperfect because several types of neoplasms have similar morphological cellular and/or tissue structures. Thus, there exists a need for systems, compositions and methods that would assist medical professionals in diagnosing neoplasms.

Although not normally visible through a light microscope typically used by a pathologist, neoplastic cells comprise biomolecules, such as proteins, that differ in the type and/or amount relative to the related normal cell. This difference can be exploited to develop specific and accurate tests to identify such neoplastic cells. The present invention provides systems, methods and compositions that allow neoplasms to be differentiated based on the type and level of expression of transcription factors present within a cell. These methods are complementary to existing morphological approaches and provide greatly improved reliability and accuracy. By making the diagnosis of neoplasms a less subjective endeavor, the present invention provides great benefits to the field of medicine, in particular, but not limited to, pathology, oncology and pharmacology.

SUMMARY

Figure 1:
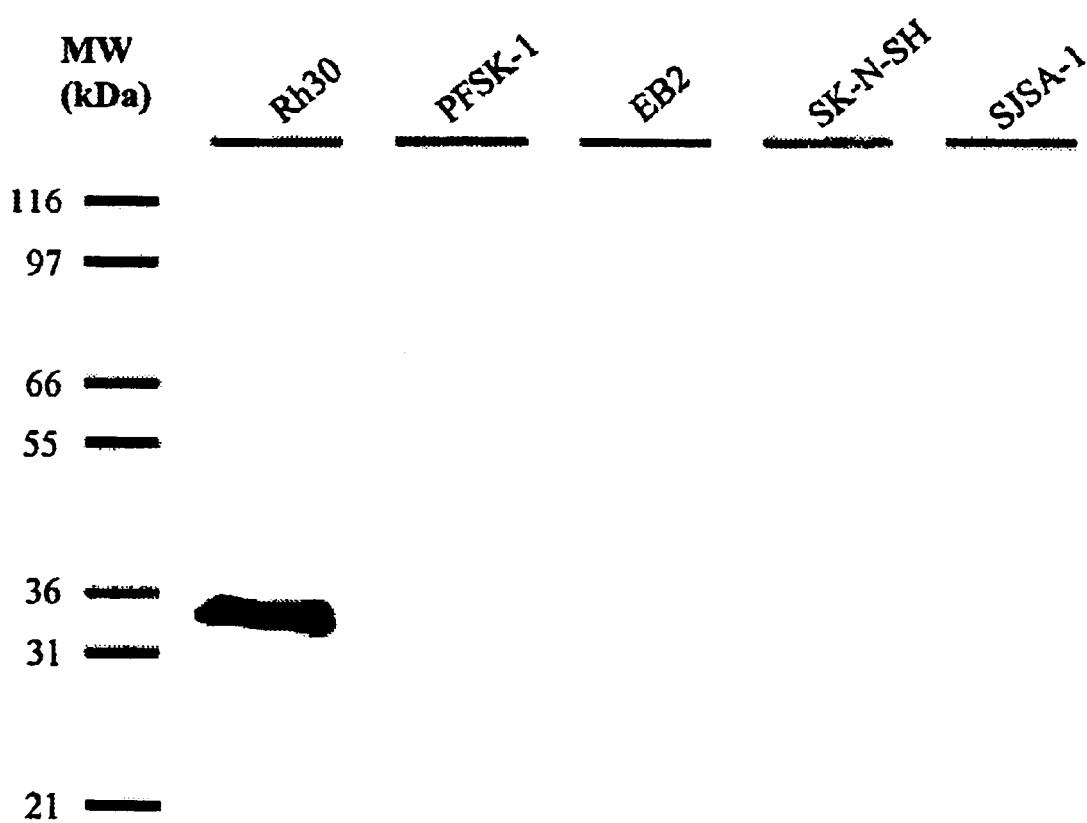
FIG. 1 depicts a western blot analysis of myogenin in various small round cell tumor cell lines using the F5D monoclonal antibody. That antibody only detectably binds with a band corresponding to the molecular size of myogenin (approximately 34 kd) in the Rh30 rhabdomyosarcoma cell lysate. All other small round cell tumor lysates did not detectably bind with that antibody. Key: Rh30=Rhabdomyosarcoma cell line; PFSK-1A=Primitive neuroectoderal tumor cell line; EB2=Lymphoma cell line; SKNSH=Neuroblastoma cell line; SJSA-1=Ewing's sarcoma cell line.
Figure 2:
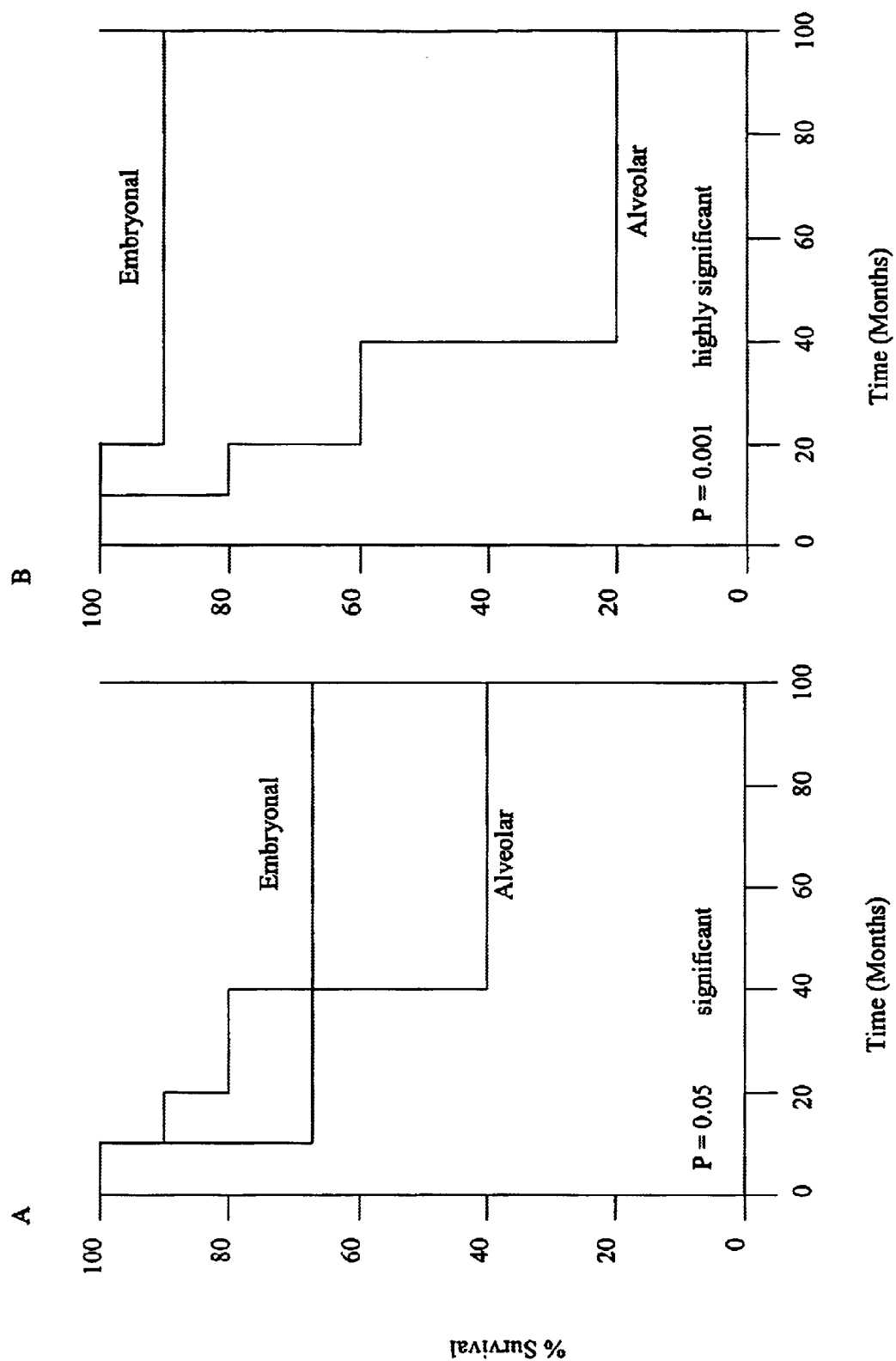
FIG. 2A and FIG. 2B depict the predicted patient survival by the Kaplan and Meier analysis based on conventional histological classification versus antibody based subclassification for myogenin and myf5 expression in tumor cells. This type of analysis is based on the finding that tumors erroneously subclassified as embryonal or alveolar rhabdomyosarcoma will cause the difference in survival between the two groups (projected survival curves for embryonal and alveolar rhabdomyosarcoma) to be less significant (FIG. 2A). A highly significant difference in survival between the embryonal and alveolar rhabdomyosarcoma that has been subclassified by anti-myf5 and anti-myogenin antibody typing is expected (FIG. 2B).

The present invention recognizes that the type and preferably amount of transcription factors expressed in cells, particularly abnormal cells such as neoplasms, is related to the differentiation state of such cells. This information can be used in a variety of contexts, such as diagnosis and prognosis of a disease process or disease state, such as cancer, and for identifying compounds that are useful for treating disease processes or disease states.

A first aspect of the present invention is composition including at least two different specific binding members that can specifically bind with at least two different transcription factors.

A second aspect of the present invention is a method of diagnosing a neoplasm such as a malignancy or prognosing the course of a neoplasm such as a malignancy or treatment thereof including contacting at least one specific binding member that can specifically bind with a transcription factor with a sample, and detecting the binding of said specific binding member with a transcription factor in said sample.

A third aspect of the present invention is a method for identifying a test compound that modulates a neoplasm such as a malignancy including contacting a sample with at least one test compound, contacting said sample with at least one specific binding member that can bind with at least one transcription factor, and detecting the binding of said at least one specific binding member with at least one transcription factor.

A fourth aspect of the present invention is a method for predicting the efficacy of a treatment for a neoplasm such as a malignancy including: contacting a sample with at least one test chemical, at least one non-chemical treatment or a combination thereof; contacting said sample with at least one specific binding member that can bind with a transcription factor; and detecting the binding of said at least one specific binding member with at least one transcription factor.

A fifth aspect of the present invention is a method for distinguishing between clinically distinct subtypes of neoplasms such as malignancy including contacting at least one specific binding member that can specifically bind with a transcription factor with a sample, and detecting the binding of said at least one specific binding member with a transcription factor in said sample.

A sixth aspect of the present invention is a monoclonal antibody that specifically binds with a member of the MyoD family of transcription factors, a leukemic transcription factor, a sex determination transcription factor or a hematopoiesis transcription factor. Such monoclonal antibody can optionally be detectably labeled.

DETAILED DESCRIPTION OF THE INVENTION

Definitions

Unless defined otherwise, all technical and scientific terms used herein have the same meaning as commonly understood by one of ordinary skill in the art to which this invention belongs. Generally, the nomenclature used herein and the laboratory procedures in cell culture, chemistry, microbiology, molecular biology, cell science and cell culture described below are well known and commonly employed in the art. Conventional methods are used for these procedures, such as those provided in the art and various general references (Sambrook et al., Molecular Cloning: A Laboratory Manual, 2nd edition, Cold Spring Harbor Press, Cold Spring Harbor, N.Y. (1989) and Ausubel et al., Current Protocols in Molecular Biology, John Wiley & Sons (1998)). Where a term is provided in the singular, the inventors also contemplate the plural of that term. The nomenclature used herein and the laboratory procedures described below are those well known and commonly employed in the art. As employed throughout the disclosure, the following terms, unless otherwise indicated, shall be understood to have the following meanings:

"Membrane permeant derivative" refers to a chemical derivative of a compound that increases membrane permeability of the compound. These derivatives are made better able to cross cell membranes because hydrophilic groups are masked to provide more hydrophobic derivatives. Also, the making groups can be designed to be cleaved from the compound within a cell to make the compound more hydrophilic once within the cell. Because the substrate is more hydrophilic than the membrane permeant derivative, it preferentially localizes within the cell (U.S. Pat. No. 5,741,657 to Tsien et al., issued Apr. 21, 1998).

"Isolated polynucleotide" refers to a polynucleotide of genomic, cDNA, or synthetic origin, or some combination thereof, which by virtue of its origin, the isolated polynucleotide (1) is not associated with the cell in which the isolated polynucleotide is found in nature, or (2) is operably linked to a polynucleotide that it is not linked to in nature. The isolated polynucleotide can optionally be linked to promoters, enhancers, or other regulatory sequences.

"Isolated protein" refers to a protein of DNA, RNA, mRNA, cDNA, recombinant RNA, or synthetic origin, or some combination thereof, which by virtue of its origin the isolated protein (1) is not associated with proteins normally found within nature, or (2) is isolated from the cell in which it normally occurs, or (3) is isolated free of other proteins from the same cellular source, for example, free of cellular proteins), or (4) is expressed by a cell from a different species, or (5) does not occur in nature.

"Polypeptide" is used herein as a generic term to refer to native protein, fragments, or analogs of a polypeptide sequence.

"Active fragment" refers to a fragment of a parent molecule, such as an organic molecule, nucleic acid molecule, or protein or polypeptide, or combinations thereof, that retains at least one activity of the parent molecule.

"Naturally occurring" refers to the fact that an object can be found in nature. For example, a polypeptide or polynucleotide sequence that is present in an organism, including viruses, that can be isolated from a source in nature and which has not been intentionally modified by man in the laboratory is naturally occurring.

"Operably linked" refers to a juxtaposition wherein the components so described are in a relationship permitting them to function in their intended manner. A control sequence operably linked to a coding sequence is ligated in such a way that expression of the coding sequence is achieved under conditions compatible with the control sequences.

"Control sequences" refer to polynucleotide sequences that affect the expression of coding and non-coding sequences to which they are ligated. The nature of such control sequences differs depending upon the host organism; in prokaryotes, such control sequences generally include promoter, ribosomal biding site, and transcription termination sequences; in eukaryotes, generally, such control sequences include promoters and transcription termination sequences. The term control sequences is intended to include components whose presence can influence expression, and can also include additional components whose presence is advantageous, for example, leader sequences and fusion partner sequences.

"Polynucleotide" refers to a polymeric form of nucleotides of a least ten bases in length, either ribonucleotides or deoxynucleotides or a modified from of either type of nucleotide. The term includes single and double stranded forms of DNA or RNA.

"Genomic polynucleotide" refers to a portion of the genome.

"Active genomic polynucleotide" or "active portion of a genome" refers to regions of a genome that can be up regulated, down regulated or both, either directly or indirectly, by a biological process.

"Directly" in the context of a biological process or processes, refers to direct causation of a process that does not require intermediate steps, usually caused by one molecule contacting or binding to another molecule (the same type or different type of molecule). For example, molecule A contacts molecule B, which causes molecule B to exert effect X that is part of a biological process.

"Indirectly" in the context of a biological process or processes, refers to indirect causation that requires intermediate steps, usually caused by two or more direct steps. For example, molecule A contacts molecule B to exert effect X which in turn causes effect Y.

"Sequence homology" refers to the proportion of base matches between two nucleic acid sequences or the proportion of amino acid matches between two amino acid sequences. When sequence homology is expressed as a percentage, for example 50%, the percentage denotes the proportion of matches of the length of sequences from a desired sequence that is compared to some other sequence. Gaps (in either of the two sequences) are permitted to maximize matching; gap lengths of 15 bases or less are usually used, 6 bases or less are preferred with 2 bases or less more preferred. When using oligonuleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and most preferably not less than 19 matches out of 20 possible base pair matches (95%).

"Selectively hybridize" refers to detectably and specifically bind. Polynucleotides, oligonucleotides and fragments thereof selectively hybridize to target nucleic acid strands, under hybridization and wash conditions that minimize appreciable amounts of detectable binding to nonspecific nucleic acids. High stringency conditions can be used to achieve selective hybridization conditions as known in the art. Generally, the nucleic acid sequence homology between the polynucleotides, oligonucleotides, and fragments thereof and a nucleic acid sequence of interest will be at least 30%, and more typically and preferably of at least 40%, 50%, 60%, 70%, 80% or 90%.

Hybridization and washing conditions are typically performed at high stringency according to conventional hybridization procedures. Typical hybridization conditions and methods are known in the art (Benton and Davis, Science 196:180 (1978); Sambrook et al., supra, (1989)).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at least 5 (in standard deviation units) using the program ALIGN with the mutation data matrix and a gap penalty of 6 or greater (Dayhoff, in Atlas of Protein Sequence and Structure, National Biomedical Research Foundation, volume 5, pp. 101–110 (1972) and Supplement 2, pp. 1–10). The two sequences or parts thereof are more preferably homologous if their amino acids are greater than or equal to 30% identical when optimally aligned using the ALIGN program.

"Corresponds to" refers to a polynucleotide sequence is homologous (for example is identical, not strictly evolutionarily related) to all or a portion of a reference polynucleotide sequence, or that a polypeptide sequence is identical to all or a portion of a reference polypeptide sequence. In contradistinction, the term "complementary to" is used herein to mean that the complementary sequence is homologous to all or a portion of a reference polynucleotide sequence. For illustration, the nucleotide sequence TATAC corresponds to a reference sequence TATAC and is complementary to a reference sequence GTATA.

The following terms are used to describe the sequence relationships between two or more polynucleotides: "reference sequence," "comparison window," "sequence identity," "percentage of sequence identity," and "substantial identity." A reference sequence is a defined sequence used as a basis for a sequence comparison; a reference sequence can be a subset of a larger sequence, for example, as a segment of a full length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides can each (1) comprise a sequence (for example a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A comparison widow, as used herein, refers to a conceptual segment of at least 20 contiguous nucleotide positions wherein a polynucleotide sequence may be compared to a reference sequence of at least 20 contiguous nucleotides and wherein the portion of the polynucleotide sequence in the comparison window can comprise additions and deletions (for example, gaps) of 20 percent or less as compared to the reference sequence (which would not comprise additions or deletions) for optimal alignment of the two sequences. Optimal alignment of sequences for aligning a comparison window can be conducted by the local homology algorithm (Smith and Waterman, Adv. Appl. Math., 2:482 (1981)), by the homology alignment algorithm (Needleman and Wunsch, J. Mol. Bio., 48:443 (1970)), by the search for similarity method (Pearson and Lipman, Proc. Natl. Acid. Sci. U.S.A. 85:2444 (1988)), by the computerized implementations of these algorithms such as GAP, BESTFIT, FASTA and TFASTA (Wisconsin Genetics Software Page Release 7.0, Genetics Computer Group, Madison, Wis.), or by inspection. Preferably, the best alignment (for example, the result having the highest percentage of homology over the comparison window) generated by the various methods is selected.

"Sequence identity" means that two polynucleotide sequences are identical (for example, on a nucleotide-by-nucleotide basis) over the window of comparison.

"Percentage of sequence identity" is calculated by comparing two optimally aligned sequences over the window of comparison, determining the number of positions at which the identical nucleic acid base occurs in both sequences to yield the number of matched positions, dividing the number of matched positions by the total number of positions in the window of comparison (for example, the window size), and multiplying the result by 100 to yield the percentage of sequence identity.

"Substantial identity" as used herein denotes a characteristic of a polynucleotide sequence, wherein the polynucleotide comprises a sequence that has at least 30 percent sequence identity, preferably at least 50 to 60 percent sequence, more usually at least 60 percent sequence identity as compared to a reference sequence over a comparison window of at least 20 nucleotide positions, frequently over a window of at least 25 to 50 nucleotides, wherein the percentage of sequence identity is calculated by comparing the reference sequence to the polynucleotide sequence that may include deletions or addition which total 20 percent or less of the reference sequence over the window of comparison.

"Substantial identity" as applied to polypeptides herein means that two peptide sequences, when optimally aligned, such as by the programs GAP or BESTFIT using default gap weights, share at least 30 percent sequence identity, preferably at least 40 percent sequence identity, and more preferably at least 50 percent sequence identity, and most preferably at lest 60 percent sequence identity. Preferably, residue positions, which are not identical, differ by conservative amino acid substitutions.

"Conservative amino acid substitutions" refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chan is cystein and methionine. Preferred conservative amino acid substitution groups are: valine-leucine-isoleucine; phenylalanine-tyrosine; lysine-arginine; alanine-valine; glutarmate-aspartate; and asparagine-glutamine.

"Modulation" refers to the capacity to either enhance or inhibit a functional property of a biological activity or process, for example, enzyme activity or receptor binding. Such enhancement or inhibition may be contingent on the occurrence of a specific event, such as activation of a signal transduction pathway and/or may be manifest only in particular cell types.

"Modulator" refers to a chemical (naturally occurring or non-naturally occurring), such as a biological macromolecule (for example, nucleic acid, protein, non-peptide or organic molecule) or an extract made from biological materials, such as prokaryotes, bacteria, eukaryotes, plants, fungi, multicellular organisms or animals, invertebrates, vertebrates, mammals and humans, including, where appropriate, extracts of: whole organisms or portions of organisms, cells, organs, tissues, fluids, whole cultures or portions of cultures, or environmental samples or portions thereof. Modulators are typically evaluated for potential activity as inhibitors or activators (directly or indirectly) of a biological process or processes (for example, agonist, partial antagonist, partial agonist, antagonist, antineoplastic, cytotoxic, inhibitors of neoplastic transformation or cell proliferation, cell proliferation promoting agents, antiviral agents, antimicrobial agents, antibacterial agents, antibiotics, and the like) by inclusion in assays described herein. The activity of a modulator may be known, unknown or partially known.

"Test chemical" or "test compound" refers to a chemical, composition or extract to be tested by at least one method of the present invention to be a putative modulator. A test chemical can be of any chemical composition, such as inorganic, organic or a biomolecule. A biomolecule can be any molecule of biological origin that is found in or produced at least in part by a cell, and include, but are not limited to polypeptides, nucleic acids, lipids, carbohydrates or combinations thereof. A test chemical is usually not known to bind to the target of interest. "Control test chemical" refers to a chemical known to bind to the target (for example, a known agonist, antagonist, partial agonist or inverse agonist). Test chemical does not typically include a chemical added to a mixture as a control condition that alters the function of the target to determine signal specificity in an assay. Such control chemicals or conditions include chemicals that (1) non-specifically or substantially disrupt protein structure (for example denaturing agents such as urea or guandium, sulfhydryl reagents such as dithiotritol and beta-mercaptoethanol), (2) generally inhibit cell metabolism (for example mitochondrial uncouples) and (3) non-specifically disrupt electrostatic or hydrophobic interactions of a protein (for example, high salt concentrations or detergents at concentrations sufficient to non-specifically disrupt hydrophobic or electrostatic interactions). The term test chemical also does not typically include chemicals known to be unsuitable for a therapeutic use for a particular indication due to toxicity of the subject. Usually, various predetermined concentrations of test chemicals are used for determining their activity. If the molecular weight of a test chemical is known, the following ranges of concentrations can be used: between about 0.001 micromolar and about 10 millimolar, preferably between about 0.01 micromolar and about 1 millimolar, more preferably between about 0.1 micromolar and about 100 micromolar. When extracts are uses a test chemicals, the concentration of test chemical used can be expressed on a weight to volume basis. Under these circumstances, the following ranges of concentrations can be used: between about 0.001 micrograms/ml and about 1 milligram/ml, preferably between about 0.01 micrograms/ml and about 100 micrograms/ml, and more preferably between about 0.1 micrograms/ml and about 10 micrograms/ml.

"Target" refers to a biochemical entity involved in a biological process. Targets are typically proteins that play a useful role in the physiology or biology of an organism. A therapeutic chemical typically binds to a target to alter or modulate its function. As used herein, targets can include, but not be limited to, cell surface receptors, G-proteins, G-protein coupled receptors, kinases, phosphatases, ion channels, lipases, phosholipases, nuclear receptors, intracellular structures, transcription factors, tubules, tubulin, and the like.

"Label," "labeled" or "detectable labeled" refers to incorporation of a detectable marker, for example by incorporation of a radiolabled compound or attachment to a polypeptide of moieties such as biotin that can be detected by the binding of a section moiety, such as marked avidin. Various methods of labeling polypeptide, nucleic acids, carbohydrates, and other biological or organic molecules are known in the art. Such labels can have a variety of readouts, such as radioactivity, fluorescence, color, chemiluminescence or other readouts known in the art or later developed. The readouts can be based on enzymatic activity, such as beta-galactosidase, beta-lactamase, horseradish peroxidase, alkaline phosphatase, luciferase; radioisotopes such as $^{3}$H, $^{14}$C, $^{35}$S, $^{125}$I or $^{131}$I); fluorescent proteins, such as green fluorescent proteins; or other fluorescent labels, such as FITC, rhodamine, and lanthanides. Where appropriate, these labels can be the product of the expression of reporter genes, as that term is understood in the art. Examples of reporter genes are beta-lactamase (U.S. Pat. No. 5,741,657 to Tsien et al., issued Apr. 21, 1998) and green fluorescent protein (U.S. Pat. No. 5,777,079 to Tsien et al., issued Jul. 7, 1998; U.S. Pat. No. 5,804,387 to Cormack et al., issued Sep. 8, 1998).

"Substantially pure" refers to an object species or activity that is the predominant species or activity present (for example on a molar basis it is more abundant than any other individual species or activities in the composition) and preferably a substantially purified fraction is a composition wherein the object species or activity comprises at least about 50 percent (on a molar, weight or activity basis) of all macromolecules or activities present. Generally, as substantially pure composition will comprise more than about 80 percent of all macromolecular species or activities present in a composition, more preferably more than about 85%, 90%, 95% and 99%. Most preferably, the object species or activity is purified to essential homogeneity, wherein contaminant species or activities cannot be detected by conventional detection methods) wherein the composition consists essentially of a single macromolecular species or activity. The inventors recognize that an activity may be caused, directly or indirectly, by a single species or a plurality of species within a composition, particularly with extracts.

"Pharmaceutical agent or drug" refers to a chemical, composition or activity capable of inducing a desired therapeutic effect when property administered by an appropriate dose, regime, route of administration, time and delivery modality.

A "bioactive compound" refers to a compound that exhibits at least one bioactivity, including but not limited to antiviral activity, antineoplastic activity, antitumor activity, anticancer cell activity, differentiation activity, anti-differentiation activity and cytotoxicity.

A "bioactivity" refers to a composition that exhibits at least one bioactivity.

A "bioactive derivative" refers to a modification of a bioactive compound or bioactivity that retains at least one characteristic bioactivity of the parent compound.

A "bioactive precursor" refers to a precursor of a bioactive compound or bioactivity that exhibits at least one characteristic activity of the resulting bioactive compound or bioactivity.

An "antineoplastic activity" refers to an activity that reduces the growth rate or number of neoplastic cells in a sample, such as a culture of cancer cells or a sample that includes at least one neoplastic cell, including a patient. Such antineoplastic activity can be directed against any type of neoplasms, including, but not limited to renal cancer, leukemia, lung cancer, colon cancer, central nervous system cancer, melanoma, ovarian cancer and breast cancer.

An "anticancer cell activity" refers to an activity that reduces the growth rate or number of cancer cells in a sample, such as a culture of cancer cells or a sample that includes at least one cancer cell, including a patient. Such anticancer cell activity can be directed against any type of cancer cell, including, but not limited to renal cancer, leukemia, lung cancer, colon cancer, central nervous system cancer, melanoma, ovarian cancer, breast cancer, soft tissue cancers and bone cancer.

An "antitumor activity" refers to an activity that reduces the growth rate or number of tumor cells in a sample, such as a culture of tumor cells or a sample that includes at least one tumor cell, including a patient. Such antitumor activity can be directed against any type of tumor or tumor cell, including, but not limited to renal tumor, lung tumor, colon tumor, central nervous system tumor, melanoma, ovarian tumor, breast tumor, soft tissue and bone.

A "differentiation activity" refers to an activity that promotes a greater degree of differentiation of a cell.

An "anti-differentiation activity" refers to an activity that promotes a lesser degree of differentiation of a cell.

A "cytotoxic activity" refers to an activity that reduces the number of viable cells in a sample, including prokaryotic cells, eukaryotic cells or both.

A "subject" or "patient" refers to a whole organism in need of treatment, such as a farm animal, companion animal or human. An "animal" refers to a non-human animal.

A "treatment" refers to a treatment for a disease state, such as a neoplasm such as a malignancy. Such treatment can include chemicals, such as chemotherapeutic agents or test compounds and/or non-chemical treatment, such as electrical pules (such as electroinnovation), magnetic fields or radiation (such as radiation therapy) (see, for example, Buonanno et al., Nucleic Acids Res. 20:539–544 (1992)).

A "specific binding member" refers to a member of a group of two or moieties that can specifically bind with each other rather than becoming non-specifically associated with each other, such as by precipitation. Examples of specific binding members include, but are not limited to, antigen-antibody, receptor-ligand and nucleic acid-nucleic acid pairs.

"Specific," "specifically," "specifically bind" or a "specific binding reaction" in the context of the binding of first specific binding member with at least one other specific binding member refers to binding that is preferential and not non-specific. Preferably, a specific binding reaction is unique for the specific binding members, but that need not be the case.

"Detectably bind" refers to the specific binding of one specific binding member with at least one other specific binding member that can be detected. For example, one specific binding member can be detectably labeled such that the detectable presence of the label indicates a specific binding event. The detection limits of such detectable binding are related to the detectable label used and the detection method or device used.

An "antibody" refers to an immunoglobulin of any class or subclass, a portion thereof or an active fragment thereof, wherein an active fragment of an antibody retains its specific binding capability. An antibody can be a polyclonal antibody, a monoclonal antibody or a mixture thereof.

A "cellular component" refers to a portion of a cell, such as an organelle or other structure, or protein or other biomolecule, that is on or within a cell.

A "transcription factor" refers to a molecule that can modulate the expression or transcription of a gene or nucleic acid sequence. Such transcription factors are known in the art, such as those described in http://transfac.gbf-braunschweig.de/TRANSFAC/cl/cl.html (Feb. 17, 1999). Transcription factors include, but are not limited to, leucine zipper factors, helix-loop-helix factors, basic-helix-loop-helix factors, helix-loop-helix/leucine zipper factors, NF-1 factors, RF-X factors, bHSH factors, Cys4 zinc finger of nuclear receptor factors, diverse Cys4 zinc finger factors, Cys2His2 zinc finger factors, Cys6 cystein-zinc cluster factors, Homeo domain factors, paired box factors, fork head/winged helix factors, heat shock factors, tryptophane cluster factors, TEA domain factors, RHR factors, p53 factors, MADS box factors, beta-barrel alpha-helix factors, TATA-binding factors, HMG factors, heteromeric CCAAT factors, Grainyhead factors, cold-shock domain factors, Runt factors, copper fist factors, HMGI(Y) factors, STAT factors and pocket domain factors. See, for example, Littlewood and Evan, Helix-Loop-Helix Transcription Factors, Third Edition, Oxford University Press, Oxford (1998); Latchman, Transcripton Factors, A Practical Approach, Second Edition, Oxford University Press, Oxford (1999); and Semenza, Transcription Factors and Human Diseases, Oxford Monographs on Medical Genetics No. 37, Oxford University Press, Oxford (1998).

A "myogenic transcription factor" refers to a factor that regulates expression of muscle specific genes and other genes associated with the muscle differentiation program, which includes but is not limited to the MyoD family of transcription factors, which includes but is not limited to myf5, MyoD (also known as myf3), myogenin (also known as myf4) or myf6.

A "leukemic transcription factor" refers to a factor that regulates expression of lymphocyte specific genes and other genes associated with the lymphocyte differentiation program, which includes but is not limited to E2A, PBX1, RBTN2, TC Ralpha/delta, PBX2, E2A, HLF, AML1, ETO, PML-RARalpha S, S/F forms, TEL, BCR, ABL, ALL, MYH11, CBFb, DEK, CAN, c-MYC, TLL1, TCRalpha, MST1, MST2, PU.1, Ikaros, E12, E47, E2-2, EBF, Pax5, ABF1, HES1, CBF, Ets 1, Wnt16, chimeric proteins including E2A/PBX1, RBTN2/TCRalpha/delata, E2A/PBX2, E2A/HLF, AML1/ETO, TEL-AML1, CBFβ-MYH11, PML-RARalphaS/S/V forms, TAL1/TCRalpha or MST1/MST2.

A "neurogenic transcription factor" refers to a factor that regulates expression of neurogenic specific genes and other genes associated with the neurogenic differentiation program, such as those described in Littlewood and Evan, supra, 1998.

A "sex determination transcription factor" refers to a factor that regulates expression of sex determination specific genes and other genes associated with sex determination programs, such as those described in Littlewood and Evan, supra, 1998.

A "hematopoiesis transcription factor" refers to a factor that regulates expression of hematopoiesis specific genes and other genes associated with the hematopoiesis differentiation program, such as those described in Littlewood and Evan, supra, 1998.

"Immobilized," such as "immobilized on a solid support" refers to a moiety, such as a macromolecule, such as a protein, or a cell, that has been either reversibly or irreversibly localized. For example, a moiety such as a protein can be irreversibly immobilized on a solid support by a variety of methods known in the art, such as by cross-linking with glutaraldehyde or other appropriate chemicals. Furthermore, a moiety such as an antigen can be reversibly immobilized by being attached to, for example, a specific binding member that is immobilized on a solid support. A solid support can be coated with a compound such that the solid support irreversibly or reversibly immobilizes a moiety. For example, a glass or plastic surface can be coated with fibronectin, which promotes the reversible immobilization of a eukaryotic cell on the solid support.

A "solid support" refers to any solid substrate in any form. For example, a solid support can be a plastic (such as polystyrene or cycloolefin polymers) a glass, a magnetic compound, a membrane (such as nylon or nitrocellulose) or other appropriate solid substrate for a particular application. A solid support can take any configuration, such as beads, sheets, tubes, plates and/or wells (such as microtiter plates), circle or columns or other configuration appropriate for a particular application.

A "neoplastic cell" or a "neoplasm" refers to a cell or a population of cells, including a tumor or tissue (including cell suspensions such as bone marrow and fluids such as blood or serum), that exhibits abnormal growth by cellular proliferation greater than normal tissue. Neoplasms can be benign or malignant.

A "benign cell" refers to a non-malignant neoplasm.

A "malignant cell" or a "malignancy" refers to a cell that is abnormal and can be classified as a malignancy. A malignant cell can be capable of metastasis under appropriate conditions. A malignancy can have a variety of subtypes, including clinically distinct subtypes, such as, for example, alveolar rhabdomyosarcoma and embryonal rhabdomyosarcoma, which have different prognoses and different responses to therapies.

A "soft malignant cell" or "soft tissue malignant cell" refers to a cell from malignancies from a solid tissue (as opposed to blood cells), excluding bone.

A "solid malignant cell" refers to a cell from a malignancy from a sold tissue, including the bone.

A "myosarcoma" refers to a malignant neoplasm derived from muscular tissue.

A "rhabdomyosarcoma" refers to a malignant neoplasm that exhibit myogenic features that can occur in the skeletal muscle, brain, heart, lung, kidney, bladder, vagina and other locations in the body. "Alveolar rhabdomyosarcoma" refers to a rhabdomyosarcoma that shows reciprocal translocations involving chromosome 12 and 13. "Embryonal rhabdomyosarcoma" refers to a rhabdomyosarcoma that frequently show deletion of chromosome 11p.

A "tissue" refers to a collection of cells as that term is known in the art. A "culture" of cells is a collection of cells as that term is known in the art and can be a clonal population of cells or a mixed population of cells. A "tumor tissue" is a collection of cells that includes at least one cell derived from at least one tumor. A "fixed tissue" is a tissue that has been fixed for evaluation, staining or viewing using a variety of methods known in the art, such as by treatment with paraformaldehyde, formaldehyde, acetone, methanol or a combination thereof.

A "cell extract" refers to a preparation that is derived from least one cell from at least one source of cells, such as from a tissue or from culture, that has been treated such that at least one cellular component of the source of cells is no longer in its natural cellular environment. For example, cell extracts can be made by rupturing cells using methods known in the art.

A "sample" includes any physical sample that includes a cell or a cell extract from a cell.

A sample can be from a biological source such as a subject or animal or a portion thereof, or from a cell culture. Samples from a biological source can be from a normal or abnormal organism (such as an organism suffering from a condition or disease state, such as a neoplasm) or portion thereof and can be from any fluid, tissue or organ, including healthy or abnormal (such as diseased or neoplastic) fluids, tissues or organs. Samples from a subject or animal can be used in the present invention as obtained from the subject or animal, processed such as by sectioning, aspiration such as for bone marrow specimens or cultured such that cells from the sample can be sustained in vitro as a primary or continuous cell culture or cell line.

"Diagnosing" such as in "diagnosing a neoplasm" refers to the determination of whether a subject comprises a disease or condition, such as a neoplasm including a malignancy or distinguishing one cancer from another.

"Prognosing" such as "prognosing the course of a neoplasm" refers to the determination or prediction of the course of a disease or condition, such as a neoplasm including a malignancy. The course of a disease or condition can be prognosed, for example, based on life expectancy or quality of life. Prognosing includes the determination of the time course of a disease or condition, with or without a treatment or treatments. In the instance where treatment(s) are contemplated, the prognosing includes "prognosing the efficacy of a treatment for a neoplasm" or "prognosing a malignancy."

"Modulates a neoplasm" refers to the ability of a test compound, test chemical, bioactivity or bioactive compound to alter the growth and subsequent clinical course of a neoplasm. For example, a test compound can modulate a neoplasm by making the prognosis of the neoplasm better or worse in terms of life expectancy or quality of life. "Modulates a malignancy" refers to the ability of a test compound, test chemical, bioactivity or bioactive compound to alter the course of a malignancy. For example, a test compound can modulate a malignancy by making the prognosis of the malignancy better or worse in terms of life expectancy or quality of life.

"Prediction the efficacy of a treatment for a neoplasm" refers to making a determination as to the efficacy of a test compound or pharmaceutical composition as at least a portion of a treatment for a neoplasm. Such a determination can be confirmed using a variety of methods, such as in vitro tests such as using cell culture models or in vivo tests, including animal models or human clinical trials. "Prediction the efficacy of a treatment for a malignancy" refers to making a determination as to the efficacy of a test compound or pharmaceutical composition as at least a portion of a treatment for a malignancy. Such a determination can be made or confirmed using a variety of methods, such as in vitro tests such as using cell culture models or in vivo tests, including animal models or human clinical trials.

A "control" or a "control sample" refers to a sample that acts as a positive or negative control as they are known in the art and as appropriate for a particular assay. A control can be performed contemporaneously with an assay or be performed at a prior or later time. The results of an assay can be compared to a control to determine the validity of the assay. Controls can also be used to produce standard curves such that the results of an assay can be semi-quantitative or quantitative in nature.

Other technical terms used herein have their ordinary meaning in the art that they are used, as exemplified by a variety of technical dictionaries, such as the McGraw-Hill Dictionary of Chemical Terms and the Stedman's Medical Dictionary.

Introduction

The present invention recognizes that the type and preferably amount of transcription factors expressed in cells, particularly abnormal cells such as any neoplasm such as cancer cells, including myosarcomas and lymphomas, is related to the growth and/or differentiation state of such cells. The present inventors have discovered that this information can be usefully used in a variety of contexts, such as diagnosis and prognosis of a disease process or disease state, such as neoplasms such as cancer, and provides superior results to existing methods. Furthermore the methods may also be used for identifying compounds that are useful for treating disease process or disease states.

As a non-limiting introduction to the breath of the present invention, the present invention includes several general and useful aspects, including:

1) a composition including at least two different specific binding members that can specifically bind with at least two different transcription factors;
2) a method of diagnosing a neoplasm such as a malignancy or prognosing the course of a neoplasm or malignancy or treatment thereof, including contacting at least one specific binding member that can specifically bind with a transcription factor with a sample, and detecting the binding of said specific binding member with a transcription factor in said sample;
3) a method for identifying a test compound that modulates a neoplasm such as a malignancy including contacting a sample with at least one test compound, contacting said sample with at least one specific binding member that can bind with at least one transcription factor, and detecting the binding of said at least one specific binding member with at least one transcription factor;
4) a method for predicting the efficacy of a treatment for a neoplasm such as a malignancy including: contacting a sample with at least one test chemical, at least one non-chemical treatment, or a combination thereof; contacting said sample with at least one specific binding member that can bind with a transcription factor; and detecting the binding of said at least one specific binding member with at least one transcription factor;
5) a method for distinguishing between clinically distinct subtypes of a type of neoplasm such as a malignancy including contacting at least one specific binding member that can specifically bind with a transcription factor with a sample, and detecting the binding of said at least one specific binding member with a transcription factor in said sample; and
6) a monoclonal antibody that can specifically bind with a member of the MyoD family of transcription factors, a leukemic transcription factor, a sex determination transcription factor or a hematopoiesis transcription factor.

These aspects of the invention, as well as others described herein, can be achieved by using the methods, articles of manufacture and compositions of matter described herein. To gain a full appreciation of the scope of the present invention, it will be further recognized that various aspects of the present invention can be combined to make desirable embodiments of the invention.

I. Specific Binding Members That Bind With Transcription Factors

The present invention includes a composition including at least two different specific binding members that can specifically bind with at least two different transcription factors.

Specific Binding Members

The present invention includes a composition that includes at least two different specific binding members that can specifically bind with at least two different transcription factors. Preferably, each specific binding member specifically binds to a single transcription factor. The composition can include between about two, about four, about six, about eight about ten, about thirty, about fifty, about seventy and about ninety different specific binding members and about three, about five, about seven, about nine about eleven about twenty, about forty, about sixty, about eighty and about one-hundred different specific binding members, preferably between about two and about ten specific binding members At least one of the specific binding members in the composition can be an antibody, such as a polyclonal antibody or a monoclonal antibody, or a portion, fragment, or active fragment thereof. The composition of the present invention can include at least one specific binding member that binds with a cellular component other than a transcription factor.

The specific binding members can specifically bind with between about two, about four, about six, about eight about ten, about thirty, about fifty, about seventy and about ninety different transcription factors and about three, about five, about seven, about nine, about eleven about twenty, about forty, about sixty, about eighty and about one-hundred different transcription factors. The compositions of the present invention can be used as reagents to profile transcription factors presence and expression levels in a sample, such as a sample that includes at least one cell or a cell extract. Such profiling can include detecting at least one of the following: the type of transcription factors, the presence of transcription factors at a detectable level or the amount of a transcription factor.

The composition of the present invention includes at least one specific binding member that can bind with a helix-loop-helix transcription factor or a basic helix-loop-helix transcription factor. Preferably, the composition of the present invention includes specific binding members that can bind with between about two, about four, about six, about eight and about ten helix-loop-helix or basic helix-loop-helix transcription factors and about three, about five, about seven, about nine and about eleven helix-loop-helix or basic helix-loop-helix transcription factors. However, greater than ten, greater than twenty, greater than thirty, greater than forty, greater than fifty, greater than sixty such specific binding members are contemplated.

The compositions of the present invention can include specific binding members in a single container or provided in two or more separate containers. The separate containers can include one or more specific binding members.

Myogenic Transcription Factors

The present invention includes compositions that include at least one specific binding member wherein at least one specific binding member specifically binds with at least one myogenic transcription factor. Preferably, the myogenic transcription factor is a member of the MyoD family of transcription factors, including, but not limited to myf5, MyoD, myogenin or myf6. Monoclonal antibodies of the present invention and those known in the art can be used in the present invention. The monoclonal antibody MyoD1 5.8A was raised against mouse MyoD1, but detectably binds with human MyoD, and can be used in the present invention (Dias et al., Cancer Res. 52:6431–6139 (1992); Wesche et al., Am. J. Surg. Pathol. 19:261–269 (1995); Tallini et al., Am. J. Pathol. 144:693–701 (1994); Parham et al., Acta Neuropathol (Berl.) 87:605–611 (1994); Rosai et al., Am. J. Surg. Pathol. 15:974–981 (1991)).

Leukemic Transcription Factors

The present invention includes compositions that include at least one specific binding member wherein at least one specific binding member can specifically bind with at least one leukemic transcription factor. Preferably, the at least one leukemic transcription factor is selected from the group consisting of E2A, PBX1, RBTN2, TC Ralpha/delta, PBX2, E2A, HLF, AML1, ETO, PML-RARalpha S, S/F forms, TEL, BCR, ABL, ALL, CBFb, DEK, CAN, c-MYC, TAL1, TCRalpha, MST1, MST2, PU.1, Ikaros, E12, E47, E2-2, EBF, Pax5, ABF1, HES1, CBF, Ets 1, Wnt16, and chimeric proteins E2A/PBX1, RBTN2/TCRalpha/delata, E2A/PBX2, E2A/HLF, CBFβ-MYH11, AML1/ETO, TEL-AML1, PML-RARalphaS/S/V forms, TAL1/TCRalpha and MST1/MST2.

Neurogenic Transcription Factors

The present invention includes compositions that include at least one specific binding member wherein at least one specific binding member can specifically bind with at least one neurogenic transcription factor, such as NeuroD1, NeuroD2, NeuroD3 and those described in Littlewood and Evan, supra, 1998 and Lee et al., Science 268:836–844 (1995).

Sex Determination Transcription Factors

The present invention includes compositions that include at least one specific binding member wherein at least one specific binding member can specifically bind with at least one sex determination transcription factor, such as those described in Littlewood and Evan, supra, 1998.

Hematopoiesis Transcription Factors

The present invention includes compositions that include at least one specific binding member wherein at least one specific binding member can specifically bind with at least one hematopoiesis transcription factor, such as those described in Littlewood and Evan, supra, 1998.

Solid Supports

The present invention also includes compositions where at least one the specific binding members is immobilized, reversibly immobilized, irreversibly immobilized or both, on a solid support. These compositions are useful for the performance of specific binding reactions on appropriate solid supports, such as immunoassays, such as (enzyme linked immuno sorbent assays (ELISAs), western blots, immunocyhtochemistry, immunohistochemistry and immunochromatographic assays as they are known in the art. The immobilized specific binding member can be unbound with its specific binding partner transcription factor, or be bound with its specific binding partner transcription factor. Such solid supports can be used in a wide variety of specific binding formats, many of which use detectably labeled specific binding reagents, such as detectably labeled antibodies or antigens. Such formats are represented by the following: Direct non-competitive assay on a solid support (U.S. Pat. Nos. 4,187,075 and 4,497,900); Competitive binding of a solid support (U.S. Pat. Nos. 4,134,792, 3,654,090, 4,478,946, 4,092,408, 4,478,946, 4,271,140, 4,288,237, 4,490,473, 4,243,749, 4,298,685, 3,839,153, 4,048,298, 4,271,140; Sequential saturation (U.S. Pat. Nos. 4,134,792, 4,271,140, 4,048,298; Displacement or release assay (U.S. Pat. Nos. 4,120,945, 4,256,725, 4,388,295, 4,434,236); One-site immunometric on solid support (U.S. Pat. Nos. 4,134,792, 3,654,090, 4,134,792, 3,850,752, 4,134,752, 4,134,792, 4,670,383, 4,332,495, 4,034,074; GB 2,084,317 and EP 0,177,191); Sandwich assays (U.S. Pat. Nos. 4,234,792, 4,376,110, 4,478,946, 4,271,140, 4,034,074, 4,271,140, 4,474,892, 4,230,683, 4,288,237, 4,098,876, 4,376,110, 4,486,530, 4,271,140, 4,343,896; see also Turgeon, Immunology and Serology in Laboratory Medicine, C.V. Mosby Co., St. Louis, 1990).

Detectably Labeled

The present invention also includes composition where at least one specific binding members such as an antibody of the present invention or active fragment thereof is detectably labeled. Specific binding members can be detectably labeled with detectable labels appropriate for a particular assay format (see, for example, Harrow, supra, 1988). The different specific binding members can be detectably labeled with the same or different detectable label. Preferably, different specific binding members are labeled with different detectable labels that can be distinguished using a method of the present invention. For example, the different labels can be different classes of labels, such as a fluorophore and a radiolabel, or can be distinguishable types of a class of label, such as different fluorophores, such as rhodamine, FITC, Texas Red™, phycoerythrin and Green Fluorescent Protein or different colors or chemiluminescence such as those produced by the action of enzyme labels such as alkaline phosphatase, glucose oxidase or horseraddish peroxidase on an appropriate substrate.

Specific Binding Members Bound to Transcription Factor

The present invention also includes specific binding members, either immobilized or not immobilized, wherein at least one of the specific binding members is bound with a transcription factor. The specific binding member can be bound with a transcription factor in any environment, such as in a biological sample, in a tissue from an organism such as a mammal, in a cell such as a eukaryotic cell including a mammalian cell, from an extract of a tissue or from an extract of a cell.

Transcription Factor is in a Cell

The present invention includes compositions where at least one of the specific binding members is bound with a transcription factor in at least one cell or in a tissue sample. The at least one cell can be from any source, including a biological sample, such as a fluid or from a tissue, or can be a cell in culture. Preferably, this aspect of the invention uses immunocytochemistry and immunohistochemistry as such methods are known in the art. Preferably, the cells are fixed or permeabilized with an appropriate reagent, such as methanol, acetone, glutaraldehyde, formaldehyde or paraformadehyde, such that specific binding members, such as antibodies, can bind with transcription factors within the cells. The binding of the specific binding member with a transcription factor can be detected using a variety of methods such as they are known in the art for a particular label. For example, radioactive labels can be detected using autoradiography and fluorescent labels can be detected using fluorescent detection methods. Enzyme labels that produce chromogens or chemiluminescence upon action of an appropriate substrate can also be used. The detection methods can include direct and indirect binding reactions that use, for example, fluorescent labels.

Types of Cells and Samples of Cells

The compositions of the present invention include cells in which a specific binding member is bound with a transcription factor in, or derived from a wide variety of cells, sariples or tissues. Generally, cells refers to mammalian cells of any type, including cells derived from tissues taken from a subject or a portion thereof or cells in culture. Cells taken from a subject or a portion thereof can be from any appropriate fluid, tissue or organ. The fluid, tissue or organ can be a normal sample or an abnormal sample. For example, the cell can be a malignant cell, and can be from a child or an adult. The malignant cell can be a soft tissue malignant cell or a solid malignant cell. The malignant cell can be a sarcoma cell, including a myosarcoma cell or rhabdomyosarcoma cell, including an alveolar rhabdomyosarcoma and/or an embryonal rhabdomyosarcoma. The malignant cell can also be of epithelial cell malignancies, leukemias or lymphomas, or solid bone tumors.

II. Method of Diagnosing a Neoplasm or Prognosing the Course of a Neoplasm

The present invention also includes a method of diagnosing a neoplasm such as a malignancy or prognosing the course of a neoplasm such as a malignancy or treatment thereof including contacting at least one specific binding member that can specifically bind with a transcription factor with a sample, and detecting the binding of said specific binding member with a transcription factor in said sample.

Method of Diagnosing a Neoplasm

A method of diagnosing a neoplasm such as a malignancy, including: contacting a composition at least one specific binding member that can specifically bind with a transcription factor with a sample, and detecting the binding of said specific binding member with a transcription factor in said sample. Preferably, the method uses a composition of the present invention that includes a pool of at least two specific binding members that specifically bind with at least two different transcription factors.

In practicing this method, a sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as a diagnostic for neoplasms such as malignancies. For example, the detectable presence, absence, type or amount of transcription factors in a sample can be compared to such a profile for a variety of cell types such as normal cells or neoplastic cells, such as malignant cells. Other types of cells can also be profiled, including normal or non-normal (such as neoplasms or malignancies) cells from a variety of tissues, fluids or organs from adult, adolescent, youth, progeny or children, newborns, fetus or embryo at any stage of development of a variety of animals, including humans.

Furthermore, the profiles of such cells can be used to determine the developmental status of a cell in the continuum between embryonic stem cells and terminally differentiated cells because the profile of transcription factors along that profile are different and characteristic of stages of development. For example, primitive mesodermal cells (multipotential embryonal cells) differentiate to myoblasts (myogenically committed proliferative stem cells). Myoblasts have members of MyoD family induced, such as Myf-5, MyoD and myogenin. Myoblasts fuse with each other to form myotubes (bi- or multinucleated syncytia) with an up-regulation of members of the MyoD family such as MyoD and myogenin. Myotubes differentiate to myofibre A(basic unit of mature muscle) with an up-regulation of MRF4 and a down-regulation of MyoD, Myf-5 and myogenin (see, Dias et al., Seminars in Diagnostic Pathology 11:3–14 (1994)). Differentiation profiles of other types of cells, such as white blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

Method of Prognosing Course of a Neoplasm

The present invention also includes a method of prognosing the course of a neoplasm such as a malignancy, including: contacting at least one specific binding member that specifically bind with a transcription factor with a sample, and detecting the binding of said at least one specific binding member with a transcription factor in said sample. Preferably, the method uses a composition of the present invention that includes at least one specific binding member that specifically bind with at least two different transcription factors.

In practicing this method, a sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as for prognosing the course of a neoplasm such as a malignancy. For example, the detectable presence, absence, type or amount of transcription factors in a sample can be compared to such a profile for a variety of cell types, such as normal cells or neoplastic cells such as malignant cells. Other types of cells can also be profiled, including normal or non-normal cells from a variety of tissues, fluids or organs from adult, adolescent, youth, progeny or children, newborns, fetus or embryo at any stage of development of a variety of animals, including humans. In addition, the profiles of such cells can be used to determine the developmental status of a cell in the continuum between embryonic stem cells and terminally differentiated cells because the profile of transcription factors along that profile are different and characteristic of stages of development. For example, primitive mesodermal cells differentiate to myoblasts, myotubes and myofibre while various members of the MyoD family of transcription factors are up- or down-regulated (see, Dias et al., Seminars in Diagnostic Pathology, 11:3–14 (1994). Differentiation profiles of other types of cells, such as while blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

The transcription factor profile of a sample can be compared to controls to determine the stage of a disease process, such as a neoplasm such as a malignancy, because the transcription factor profile of a sample having a disease process that may change over time. The stage of disease process is related to its expected course in terms of, for example, life expectancy or quality of life. Thus, the results of the present invention can be used to prognose the course of a disease process, such as a malignancy.

Method of Prognosing the Efficacy of a Treatment

The present invention includes a method of prognosing the efficacy of a treatment for a neoplasm such as a malignancy, comprising: contacting at least one specific binding member that can specifically bind with a transcription factors with a sample, and detecting the binding of said specific binding member with a transcription factor in said sample. Preferably, the method uses a composition of the present invention that includes at least two specific binding members that specifically bind with at least two different transcription factors.

In practicing this method, a sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used to prognose the efficacy of a treatment for a neoplasm such as a malignancy. For example, the detectable presence, absence, type or amount of transcription factors in a sample can be compared to such a profile for a variety of cell types, such as normal cells or neoplastic cells such as malignant cells. Other types of cells can also be profiled, including normal or non-normal cells from a variety of tissues, fluids or organs from adult, adolescent, youth, progeny or children, newborns, fetus or embryo at any stage of development of a variety of animals, including humans. In addition, the profiles of such cells can be used to determine the developmental status of a cell in the continuum between embryonic stem cells and terminally differentiated cells or tissues because the profile of transcription factors along that profile or pathway are different and characteristic of stages of development. For example, primitive mesodermal cells differentiate to myoblasts, myotubes and myofibre while various members of the MyoD family of transcription factors are up- or down-regulated (see, Dias et al., Seminars in Diagnostic Pathology, 11:3–14 (1994). Differentiation profiles of other types of cells, such as while blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

The transcription factor profile of a sample can be compared to controls to determine the type of a disease process or the stage of a disease process, such as a neoplasm such as a malignancy, because the transcription factor profile of a sample having a disease process may change over the course of the disease process and are characteristic of a disease process. The stage of disease process is related to its expected course in terms of, for example, response to treatments, such as radiotherapy, chemotherapy or combinations thereof. Thus, the results of the present invention can be used to prognose the efficacy of a treatment directed towards a disease process, such as a neoplasm such as a malignancy.

III. Method for Identifying Test Compounds and Therapies

The present invention also includes method for identifying a test compound or therapy that modulates a neoplasm such as a malignancy including: contacting a sample with at least one test compound or at least one test therapy or a combination thereof, contacting said sample with at least one specific binding member that can bind with at least one transcription factor, and detecting the binding of said at least one specific binding member with at least one transcription factor.

Methods of Identifying Compounds

A method for identifying a test compound that modulates a neoplasm such as a malignancy, comprising: contacting a sample with at least one test compound at least one test therapy or a combination thereof; contacting said sample with at least one specific binding member that can bind with at least one transcription factor; and detecting the binding of said at least one specific binding member with at least one transcription factor. Preferably, the method uses a composition of the present invention that includes at least two specific binding members that specifically bind with at least two different transcription factors.

In practicing this method, a sample is contacted with at least one test compound or at least one test therapy or a combination thereof, wherein a transcription factor profile of the sample has or has not been previously determined, but preferably has been previously determined. This sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody (or a second binding member that is labeled, such as streptavidin that is labeled with a fluorochrome or enzyme that binds with a biotinylated primary antibody) that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as a diagnostic for malignancies. For example, the detectable presence, absence, type or amount of transcription factors in a sample can be compared to such a profile for a variety of cell types, such as normal cells or neoplastic cells such as malignant cells. Other types of cells can also be profiled, including normal or non-normal cells from a variety of tissues, fluids or organs from adult, adolescent, youth, progeny or children, newborns, fetus or embryo at any stage of development of a variety of subjects, including animals and humans. In addition, the profiles of such cells can be used to determine the developmental status of a cell in the continuum between embryonic stem cells and terminally differentiated cells because the profile of transcription factors along that profile are different and characteristic of stages of development. For example, primitive mesodermal cells differentiate to myoblasts, myotubes and myofibre while various members of the MyoD family of transcription factors are up- or down-regulated (see, Dias et al., Seminars in Diagnostic Pathology, 11:3–14 (1994). Differentiation profiles of other types of cells, such as while blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

The transcription factor profile of a sample can be compared to controls, including the transcription factor profile of the sample prior to being contacted with a test compound or a test treatment or a combination thereof, to determine the responsiveness of the sample to a test compound or a test therapy or a combination thereof. Preferably, a test compound or a test therapy or a combination thereof will alter the transcription profile of a sample from a less differentiated state to a more differentiated state which results in a reduction in the neoplastic characteristic of the sample. Alternatively, a test compound or a test therapy or combination thereof will alter the transcription profile of a sample from a more differentiated state to a less differentiated state which can make cells in the sample more susceptible to treatments that preferentially kill proliferating cells. Compounds or therapies or combinations thereof that can promote transcription factor profiles that are indicative of a more differentiated state have presumptive therapeutic activity or therapies as anti-neoplastic agents, particularly for neoplasms that are characterized as being in the form of a less differentiated state.

The present invention also includes compounds and therapies identified by this method. The compound or therapy, if appropriate, can be provided in a pharmaceutically acceptable carrier. The compound or therapy, if appropriate, identified by this method can be a pharmaceutical composition and provided in an appropriate form, dose, pharmaceutically acceptable carrier and/or container or packaging. Such container or packaging can include appropriate instructions for the administration of the pharmaceutical composition or use of the therapy, including route of administration, dose, regime and related precautions.

The following sections are directed towards pharmacology and toxicology, particularly methods in these fields. These methods can be applicable to therapies as well as test compounds, compounds and/or pharmaceuticals.

Pharmacology and Toxicity of Test Compounds and Therapies

The structure of a test compound can be determined or confirmed by methods known in the art, such as mass spectroscopy. For test compounds stored for extended periods of time under a variety of conditions, the structure, activity and potency thereof can be confirmed.

Identified test compounds can be evaluated for a particular activity using art-recognized methods and those disclosed herein. For example, if an identified test compounds is found to have anticancer cell activity in vitro, then the test compound would have presumptive pharmacological properties as a chemotherapeutic to treat cancer. Such nexuses are known in the art for several disease states, and more are expected to be discovered over time. Based on such nexuses, appropriate confirmatory in vitro and in vivo models of pharmacological activity, and toxicology, and be selected and performed. The methods described herein can also be used to assess pharmacological selectivity and specificity, and toxicity.

Identified test compounds can be evaluated for toxicological effects using known methods (see, Lu, Basic Toxicology, Fundamentals, Target Organs, and Risk Assessment, Hemisphere Publishing Corp., Washington (1985); U.S. Pat. No. 5,196,313 to Culbreth (issued Mar. 23, 1993) and U.S. 5,567,952 to Benet (issued Oct. 22, 1996)). For example, toxicology of a test compound can be established by determining in vitro toxicity towards a cell line, such as a mammalian, for example human, cell line. Test compounds can be treated with, for example, tissue extracts, such as preparations of liver, such as microsomal preparations, to determine increased or decreased toxicological properties of the test compound after being metabolized by a whole organism. The results of these types of studies are predictive of toxicological properties of chemical s in animals, such as mammals, including humans.

Alternatively, or in addition to these in vitro studies, the toxicological properties of a test compound in an animal model, such as mice, rats, rabbits, dogs or monkeys, can be determined using established methods (see, Lu, supra (1985); and Creasey, Drug Disposition in Humans, The Basis of Clinical Pharmacology, Oxford University Press, Oxford (1979)). Depending on the toxicity, target organ, tissue, locus and presumptive mechanism of the test compound, the skilled artisan would not be burdened to determine appropriate doses, $LD_{50}$ values, routes of administration and regimes that would be appropriate to determine the toxicological properties of the test compound. In addition to animal models, human clinical trials can be performed following established procedures, such as those set forth by the United States Food and Drug Administration (USFDA) or equivalents of other governments. These toxicity studies provide the basis for determining the efficacy of a test compound in vivo.

Efficacy of Test Compounds

Efficacy of a test compound can be established using several art recognized methods, such as in vitro methods, animal models or human clinical trials (see, Creasey, supra (1979)). Recognized in vitro models exist for several diseases or conditions. For example, the ability of a compound or composition to extend the life-span of HIV-infected cells in vitro is recognized as an acceptable model to identify chemicals expected to be efficacious to treat HIV infection or AIDS (see, Daluge et al., Antimicro. Agents Chemother. 41:1082–1093 (1995)). Furthermore, the ability of cyclosporin A (CsA) to prevent proliferation of T-cells in vitro has been established as an acceptable model to identify chemicals expected to be efficacious as immunosuppressants (see, Suthanthiran et al., supra (1996)). For nearly every class of therapeutic, disease or condition, an acceptable in vitro or animal model is available. In addition, these in vitro methods can use tissue extracts, such as preparations of liver, such as microsomal preparations, to provide a reliable indication of the effects of metabolism on a bioactive compound or bioactivity. Similarly, acceptable animal models can be used to establish efficacy of test compounds to treat various diseases or conditions. For example, the rabbit knee is an accepted model for testing agents for efficacy in treating arthritis (see, Shaw and Lacy, J. Bone Joint Surg. (Br.) 55:197–205 (1973)). Hydrocortisone, which is approved for use in humans to treat arthritis, is efficacious in this model which confirms the validity of this model (see, McDonough, Phys. Ther. 62:835–839 (1982)). When choosing an appropriate model to determine efficacy of bioactive compounds and bioactivities, the skilled artisan can be guided by the state of the art to choose an appropriate model, doses and route of administration, regime and endpoint and as such would not be unduly burdened.

In addition to animal models, human clinical trials can be used to determine the efficacy of test compounds. The USFDA, or equivalent governmental agencies, have established procedures for such studies.

Selectivity of Test Compounds

The in vitro and in vivo methods described above also establish the selectivity of a candidate modulator. It is recognized that chemicals can modulate a wide variety of biological processes or be selective. Panels of cells as they are known in the art can be used to determine the specificity of a test compound (WO 98/13353 to Whitney et al., published Apr. 2, 1998). Selectivity is evident, for example, in the field of chemotherapy, where the selectivity of a chemical to be toxic towards cancerous cells, but not towards non-cancerous cells, is obviously desirable. Selective modulators are preferable because they have fewer side effects in the clinical setting. The selectivity of a test compound can be established in vitro by testing the toxicity and effect of a test compound can be established in vitro by testing the toxicity and effect of a test compound on a plurality of cell lines that exhibit a variety of cellular pathways and sensitivities. The data obtained form these in vitro toxicity studies can be extended to animal model studies, including human clinical trials, to determine toxicity, efficacy and selectivity of a test compound.

The selectivity, specificity and toxicology, as well as the general pharmacology, of a test compound can often improved by generating additional test chemicals based on the structure/property relationship of a test compound originally identified as having activity. Test compounds can be modified to improve various properties, such as affinity, life-time in blood, toxicology, specificity and membrane permeability. Such refined test compounds can be subjected to additional assays as they are known in the art or described herein. Methods for generating and analyzing such compounds or compositions are known in the art, such as U.S. Pat. No. 5,574,656 to Agrafiotis et al.

Pharmaceutical Compositions

The present invention also encompasses a test compound in a pharmaceutical composition comprising a pharmaceutically acceptable carrier prepared for storage and preferably subsequent administration, which have a pharmaceutically effective amount of the test compound in a pharmaceutically acceptable carrier or diluent. Acceptable carriers or diluents for therapeutic use are well known in the pharmaceutical art, and are described, for example, in Remington's Pharmaceutical Sciences, Mack Publishing Co., (A. R. Gennaro edit. (1985)). Preservatives, stabilizers, dyes and even flavoring agents can be provided in the pharmaceutical composition. For example, sodium benzoate, sorbic acid and esters of p-hydroxybenzoic acid can be added as preservatives. In addition, antioxidants and suspending agents can be used.

The test compounds of the present invention can be formulated and used as tablets, capsules or elixirs for oral administration; suppositories for rectal administration; sterile solutions, suspensions or injectable administration; and the like. Injectables can be prepared in conventional forms either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride and the like. In addition, if desired, the injectable pharmaceutical compositions can contain minor amounts of nontoxic auxiliary substances, such as wetting agents, pH buffering agents and the like. If desired, absorption enhancing preparation, such as liposomes, can be used.

The pharmaceutically effective amount of a test compound required as a dose will depend on the route of administration, the type of animal or patient being treated, and the physical characteristics of the specific animal under consideration. The dose can be tailored to achieve a desired effect, but will depend on such factors as weight, diet, concurrent medication and other factors which those skilled in the medical arts will recognize. In practicing the methods of the present invention, the pharmaceutical compositions can be used alone or in combination with one another, or in combination with other therapeutic or diagnostic agents. These products can be utilized in vivo, preferably in a mammalian patient, preferably in a human, or in vitro. In employing them in vivo, the pharmaceutical compositions can be administered to the patient in a variety of ways, including parenterally, intravenously, subcutaneously, intramuscularly, colonically, rectally, nasally or intraperitoneally, employing a variety of dosage forms. Such methods can also be used in testing the activity of test compounds in vivo.

As will be readily apparent to one skilled in the art, the useful in vivo dosage to be administered and the particular mode of administration will vary depending upon the age, weight and type of patient being treated, the particular pharmaceutical composition employed, and the specific use for which the pharmaceutical composition is employed. The determination of effective dosage levels, that is the dose levels necessary to achieve the desired result, can be accomplished by one skilled in the art using routine methods as discussed above. Typically, human clinical applications of products are commenced at lower dosage levels, with dosage level being increased until the desired effect is achieved. Alternatively, acceptable in vitro studies can be used to establish useful doses and routes of administration of the test compound.

In non-human animal studies, applications of the pharmaceutical compositions are commenced at higher dose levels, with the dosage being decreased until the desired effect is no longer achieved or adverse side effects are reduced of disappear. The dosage for the test compounds of the present invention can range broadly depending upon the desired affects, the therapeutic indication, route of administration and purity and activity of the test compound. Typically, dosages can be between about 1 ng/kg and about 10 ng/kg, preferably between about 10 ng/kg and about 1 mg/kg, more preferably between about 100 ng/kg and about 100 micrograms/kg, and most preferably between about 1 microgram/kg and about 10 micrograms/kg.

The exact formulation, route of administration and dosage can be chosen by the individual physician in view of the patient's condition (see, Fingle et al., in The Pharmacological Basis of Therapeutics (1975)). It should be noted that the attending physician would know how to and when to terminate, interrupt or adjust administration due to toxicity, organ dysfunction or other adverse effects. Conversely, the attending physician would also know to adjust treatment to higher levels if the clinical response were not adequate. The magnitude of an administrated does in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight and response of the individual patient, including those for veterinary applications.

Depending on the specific conditions being treated, such pharmaceutical compositions can be formulated and administered systemically or locally. Techniques for formation and administration can be found in Remington's Pharmaceutical Sciences, 18th Ed., Mack Publishing Co., Easton, Pa. (1990). Suitable routes of administration can include oral, rectal, transdermal, otic, ocular, vaginal, transmucosal or intestinal administration; parenteral delivery, including intramuscular, subcutaneous, intramedullary injections, as well as intrathecal, direct intraventricular, intravenous, intraperitoneal, intranasal, or intraocular injections.

For injection, the pharmaceutical compositions of the present invention can be formulated in aqueous solutions, preferably in physiologically compatible buffers such as Hanks' solution, Ringer's solution or physiological saline buffer. For such transmucosal administration, penetrans appropriate to the barrier to be permeated are used in the formulation. Such penetrans are generally known in the art.

Use of pharmaceutically acceptable carriers to formulate the pharmaceutical compositions herein disclosed for the practice of the invention into dosages suitable for systemic administration is within the scope of the invention. With proper choice of carrier and suitable manufacturing practice, the compositions of the present invention, in particular, those formulation as solutions, can be administered parenterally, such as by intravenous injection. The pharmaceutical compositions can be formulated readily using pharmaceutically acceptable carriers well known in the art into dosages suitable for oral administrations. Such carriers enable the bioactive compounds and bioactivities of the invention to be formulated as tables, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Substantially all molecules present in an aqueous solution at the time of liposome formation are incorporated into or within the liposomes thus formed. The liposomal contents are both protected from the external microenvironment and, because liposomes fuse will cell membranes, are efficiently delivered into the cell cytoplasm. Additionally, due to their hydrophobicity, small organic molecules can be directly administered intracellularly.

Pharmaceutical compositions suitable for use in the present invention include compositions wherein the active ingredients are contained in an effective amount to achieve its intended purpose. Determination of the effective amount of a pharmaceutical composition is well within the capability of those skilled in the art, especially in light of the detailed disclosure provided herein. In addition to the active ingredients, these pharmaceutical compositions can contain suitable pharmaceutically acceptable carriers comprising excipients and auxiliaries which facilitate processing of the active chemicals into preparations which can be used pharmaceutically. The preparations formulated for oral administration may be in the form of tables, dragees, capsules or solutions. The pharmaceutical compositions of the present invention can be manufactured in a manner that is itself known, for example by means of conventional mixing, dissolving, granulating, dragee-making, emulsifying, encapsulating, entrapping or lyophilizing processes. Pharmaceutical formulations for parenteral administration include aqueous solutions of active chemicals in water-soluble form.

Additionally, suspensions of the active chemicals may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances what increase the viscosity of the suspension, such as sodium carboxymethyl cellulose, sorbitol or dextran. Optionally, the suspension can also contain suitable stabilizers or agents that increase the solubility of the chemicals to allow for the preparation of highly concentrated solutions.

Pharmaceutical compositions for oral use can be obtained by combining the active chemicals with solid excipient, optionally grinding a resulting mixture, and processing the mixture of granules, after adding suitable auxiliaries, if desired, to obtain tables or dragee cores. Suitable excipients are, in particular, fillers such as sugars, including lactose, sucrose, mannitol or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose and/or polyvinylpyrrolidone. If desired, disintegrating agents can be added, such as the cross-linked polyvinyl pyrolidone, agar, alginic acid or a salt thereof such as sodium alginate. Dragee cores can be provided with suitable coatings. Dyes or pigments can be added to the tablets or dragee coatings for identification or to characterize different combinations of active doses.

Systems

The present invention also includes a system that includes a test compound that can be used to practice at least one method of the present invention. Such systems can include a storage station, a dispensation station, a detector station, and a computing station, each of which can be separate or combined. A storage station stores at least one reagent for use in a method, such as cells, buffers and test compounds. The dispensation station dispenses such reagents into a receptacle for use in the method, such as a microtiter plate. The detector station includes a detector to detect the readout of the method, such as radioactivity or fluorescence. The computing station is directly or indirectly connected to the detection station and obtains data therefrom. The computing station comprises computer hardware and software to process the data obtained from the detector station and can also monitor and control the storage station, dispensation station and detector station (see, U.S. Pat. No. 5,670,113 to Akong, issued Sep. 23, 1997; WO 98/52047 to Stylli et al., published Nov. 19, 1998).

IV. Method for Predicting the Efficacy of a Compound or Treatment

The present invention also includes method for predicting the efficacy of a treatment for a neoplasm such as a malignancy including: contacting a sample with at least one test chemical, at least one non-chemical treatment, or a combination thereof; contacting said sample with at least one specific binding member that binds with a transcription factor, and detecting the binding of said at least one specific binding member with at least one transcription factor.

Methods of Predicting Efficacy of Compounds and Treatments Using a Sample From a Subject The present invention includes a method for predicting the efficacy of a treatment for a neoplasm such as a malignancy, including: contacting a sample with at least one test chemical at least one treatment or a combination thereof; contacting the sample with at least one specific binding member that binds with a transcription factor; and detecting the binding of the at least one specific binding member with at least one transcription factor. Preferably, the method uses a composition of the present invention that includes at least two specific binding members that specifically bind with at least two different transcription factors. The sample is preferably obtained from a subject for which a proposed treatment or plurality of treatments is proposed. The results of this test can be used to select treatments that have a greater likelihood of success in reducing the severity or duration of a disease state and/or increasing the life expectancy of quality of life of a subject.

In practicing this method, a sample is contacted with a test compound, treatment or combination thereof wherein a transcription factor profile of the sample has or has not been previously determined, but preferably has been previously determined. This sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as a diagnostic for malignancies. For example, the detectable presence, absence, type or amount of transcription factors in a sample can be compared to such a profile for a variety of cell types, such as normal cells or neoplastic cells such as malignant cells. Other types of cells can also be profiled, including normal or non-normal cells from a variety of tissues, fluids or organs from adult, adolescent, youth, progeny or children, newborns, fetus or embryo at any stage of development of a variety of animals, including humans. In addition, the profiles of such cells can be used to determine the developmental status of a cell in the continuum between embryonic stem cells and terminally differentiated cells because the profile of transcription factors along that profile are different and characteristic of stages of development. For example, primitive mesodermal cells differentiate to myoblasts, myotubes and myofibre while various members of the MyoD family of transcription factors are up- or down-regulated (see, Dias et al., Seminars in Diagnostic Pathology, 11:3–14 (1994). Differentiation profiles of other types of cells, such as while blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

The transcription factor profile of a sample can be compared to controls, including the transcription factor profile of the sample prior to being contacted with a test compound, to determine the responsiveness of the sample to a test compound or test treatment or combination thereof. Preferably, a test compound or test treatment or combination thereof will alter the transcription profile of a sample from a less differentiated state to a more differentiated state, but the reverse may also be true. Compounds, treatments or combinations thereof that can promote transcription factor profiles that are indicative of a more differentiated state have a greater probability of being effective against the neoplasm in the sample. Different subjects and different neoplasms have different responsiveness to a variety of compounds, treatments and combinations thereof. By preselecting proposed compounds, treatments or combinations thereof for a subject in this manner, a treatment that has a relatively high likelihood of success can be prechosen prior to administering of potentially damaging or ineffective compounds, treatments or combinations thereof to a subject.

The present invention also includes compounds, treatments or combinations thereof identified by this method. The compound or treatment or combination thereof, if appropriate, can be provided in a pharmaceutically acceptable carrier. The compound or treatment or combination thereof, if appropriate, can be a pharmaceutical composition and provided in an appropriate form, dose, pharmaceutically acceptable carrier and/or container or packaging. Such container or packaging can include appropriate instructions for the administration of the pharmaceutical composition or treatment or combination thereof, including route of administration, dose, regime and related precautions.

Methods of Predicting Efficacy of pharmaceutical Composition or Treatments

A method for predicting the efficacy of a treatment for a neoplasm such as a malignancy, including: contacting a sample with at least one pharmaceutical composition or at least one non-chemical treatment or a combination thereof; contacting said sample with at least one specific binding member that binds with a transcription factor; and detecting the binding of said at least one specific binding member with at least one transcription factor. Preferably the pharmaceutical composition or treatment or combination thereof is known to be safe and efficacious for a particular purpose, but the applicability of the pharmaceutical composition to a neoplasm (either generally or to a particular neoplasm) is not known. Preferably, the method uses a composition of the present invention that includes at least two specific binding members that specifically bind with at least two different transcription factors. The sample can be any sample and can be obtained from a subject for which a proposed therapy, chemotherapy, treatment or plurality of treatments is proposed. When the sample is from a subject, the results of this test can be used to select chemical and/or non-chemical treatments that have a greater likelihood of success in reducing the severity or duration of a disease state and/or increasing the life expectancy of quality of life of a subject.

In practicing this method, a sample is contacted with at least one pharmaceutical composition or at least one treatment or a combination thereof, wherein a transcription factor profile of the sample has or has not been previously determined, but preferably has been previously determined. This sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as a diagnostic for neoplasms such as malignancies. For example, the detectable presence, absence, type or amount of transcription factors in a sample can be compared to such a profile for a variety of cell types, such as normal cells or neoplastic cells such as malignant cells. Other types of cells can also be profiled, including normal or non-normal cells from a variety of tissues, fluids or organs from adult, adolescent, youth, progeny or children, newborns, fetus or embryo at any stage of development of a variety of animals, including humans. In addition, the profiles of such cells can be used to determine the developmental status of a cell in the continuum between embryonic stem cells and terminally differentiated cells because the profile of transcription factors along that profile are different and characteristic of stages of development. For example, primitive. mesodermal cells differentiate to myoblasts, myotubes and myofibre while various members of the MyoD family of transcription factors are up- or down-regulated (see, Dias et al., Seminars in Diagnostic Pathology, 11:3–14 (1994). Differentiation profiles of other types of cells, such as while blood cells, are also characterized (Roitt et al., Immunology, Third Ed., Mosby, St. Louis (1993)). The present invention includes these recited cell types and all cell types, including those of mesodermal, ectodermal and endodermal origin that have a differentiation profile. Profiles of transcription factors in these cells along a differentiation pathway can be used as controls, both positive and negative, in order to compare the profile of transcription factors of a sample being analyzed using the methods of the present invention. Such controls can be performed at the same or different time as the sample being analyzed.

The transcription factor profile of a sample can be compared to controls, including the transcription factor profile of the sample prior to being contacted with a pharmaceutical composition, to determine the responsiveness of the sample to a pharmaceutical composition, treatment or combination thereof. Preferably, a test compound or treatment or combination thereof will alter the transcription profile of a sample from a less differentiated state to a more differentiated state, but the reverse may also be true. Compounds or treatments or combinations thereof that can promote transcription factor profiles that are indicative of a more differentiated state have presumptive therapeutic activity as antineoplastic agents or treatments, particularly for neoplasms that are characterized as being in the form of a less differentiated state. Different subjects and different neoplasms have different responsiveness to a variety of pharmaceutical compositions. By prescreening proposed treatments for a subject in this manner, a pharmaceutical composition that has a relatively high likelihood of success can be preselected prior to administering of potentially damaging or ineffective compounds to a subject.

In addition, the amount of pharmaceutical composition or treatment or combination thereof effective to cause a shift in transcription factor profiles from a less differentiated state to a more differentiated state can be determined by using a variety of concentrations of a pharmaceutical composition or treatment or combination thereof in this method. In addition, pharmaceutical compositions that include a plurality of pharmaceutical agents can be evaluated using this method. Furthermore, pharmaceutical compositions that are not or have not been considered useful as a treatment for a disease state, such as a neoplasm such as a malignancy can be evaluated using this method. In this case, in particular, new uses for existing pharmaceutical compositions can be identified using the methods of the present invention.

The present invention also includes pharmaceutical compositions or treatments or combinations thereof identified by this method. The compound or treatment or combination thereof, if appropriate, can be provided in a pharmaceutically acceptable carrier. The compound or treatment or combination thereof identified by this method, if appropriate, can be a pharmaceutical composition and provided in an appropriate form, dose, pharmaceutically acceptable carrier and/or container or packaging. Such container or packaging can include appropriate instructions for the administration of the pharmaceutical composition or therapy or combination thereof including route of administration, dose, regime and related precautions.

V. Methods for Distinguishing Different Sub-Types or Sub-Classes of Neoplasms The present invention also includes a method for distinguishing between clinically distinct subtypes or subclasses of a type of neoplasm such as a malignancy including contacting at least one specific binding member that can specifically bind with a transcription factor with a sample, and detecting the binding of said at least one specific binding member with a transcription factor in said sample. Preferably, the method uses a composition of the present invention that includes at least two specific binding members that specifically bind with at least two different transcription factors.

In practicing this method, a sample is contacted with a composition that includes at least one specific binding member (such as an antibody) that specifically binds with a transcription factor. Preferably, the composition is a composition of the present invention. The binding of the at least one specific binding member to a transcription factor in the sample can be detected using a variety of methods as they are known in the art and disclosed herein, such as direct or indirect detection methods. For example, a specific binding member, such as an antibody, can be detectably labeled such that the binding of the specific binding member to a transcription factor can be directly determined. In the alternative, the binding of a specific binding member to a transcription factor can be determined by indirect methods, such as using a detectably labeled antibody that binds with a specific binding member.

The detectable presence, absence, type or amount of transcription factors in a sample can be determined using this method. The relative detectable presence, absence, type or amount of transcription factors in a sample can provide a profile of transcription factors in the sample. The profile of one or more transcription factors in a sample can be used as a diagnostic for malignancies, including subtypes of malignancies such as clinically distinct subtypes of malignancies. For example, the detectable presence, absence, type or amount of transcription factors in a sample can be compared to such a profile for a variety of cell types, such as normal cells or malignant cells. Profiles of transcription factors in these cells can be used as controls, both positive and negative, in order to compare the profile of transcription factors of a sample being analyzed using the methods of the present invention. Such controls can be performed at the same or different time as the sample being analyzed.

VI. Monoclonal Antibodies

The present invention also includes an optionally detectably labeled monoclonal antibody that specifically binds with a member of the MyoD family of transcription factors, a leukemic leukemic transcription factor, a sex determination transcription factor or a hematopoiesis transcription factor.

Particular Monoclonal Antibodies

The present invention also includes monoclonal antibodies that specifically bind or detectably bind with the transcription factor myf5 or myf6 and hybridoma cell lines that produce such monoclonal antibodies. The present invention also includes monoclonal antibodies that specifically bind or detectably bind with the leukemic transcription factor E2A, PBX1, RBTN2, TC Ralpha/delta, PBX2, E2A, HLF, AML1, ETO, PML-RARalpha S, S/F forms, TEL, BCR, ABL, ALL, MYH11, CBFb, DEK, CAN, c-MYC, TLL1, TCRalpha, MST1, MST2, PU.1, Ikaros, E12, E47, E2-2, EBF, Pax5, ABF1, HES1, CBF, Ets 1, Wnt16, chimeric proteins including E2A/PBX1, RBTN2/TCRalpha/delata, E2A/PBX2, E2A/HLF, AML1/ETO, TEL-AML1, CBFβ-MYH11, PML-RARalphaS/S/V forms, TAL1/TCRalpha or MST1/MST2.

These monoclonal antibodies detectably bind with either myf5 or myf6 and do not detectably bind with other members of the MyoD family of transcription factors. Preferably, the detection system used is an enzymatic label such as horseradish peroxidase using a detection substrate of diaminobenzadine, but other detectable labels such as fluorophores can be used.

VII. Detection of Transcription Factor Profiles Using Nucleic Acid Molecules The present invention includes the methods and compositions discussed herein which utilize nucleic acid molecules and associated detection methods and hybridization methods rather than specific binding members. In particular, nucleic acid molecules can be used to detect and profile transcription factors in a sample.

For example, nucleic acid molecules that selectively and detectably hybridize with a nucleic acid that encodes a transcription factor can be used to detect nucleic acids that encode a transcription factor in a cell or a cell lysate using established methods (Sambrook et al., Molecular Cloning, A Laboratory Manual, Cold Spring Harbor Press (1989)). For example, a nucleic acid molecule, such as single stranded DNA or RNA molecule, that hybridizes with a mRNA that encodes a transcription factor can be detectably labeled. Such a detectably labeled nucleic acid molecule can be contacted with a cell or an extract of a cell to detect the presence and amount of nucleic acids that encode a transcription factor in a cell. The amount of nucleic acids that encode a transcription factor in a sample correlates well with the expression of a transcription factor in a cell, especially when the nucleic acids that encode a transcription factor are mRNA. Nucleic acid molecules in a cell or a cell extract can be detected using established methods, including in situ hybridization, northern blot methods, southern blot methods, and PCR methods.

The selection of appropriate nucleic acid molecules for use as probes can be made by determining the nucleic acid sequence of a target transcription factor, such as from the literature, and determining an appropriate nucleic acid sequence, length and label to detect a nucleic acid molecule, including DNA and/or RNA that encodes target transcription factor. Modifications to the length and sequence of sequences identified in the literature can be modified as to length, sequence homology, sequence identity, percentage of sequence identity and substantial identity. Computer programs known in the art, such as BLAST, are preferred for the selection process. The ability of a nucleic acid molecule to selectively hybridize with a target nucleic acid molecule can be confirmed using hybridization methods known in the art (Sambrook et al., supra, 1989)).

As with specific binding members, a plurality of nucleic acid molecules can be used to detect and profile transcription factors. A plurality of nucleic acid molecules can be used to detect a plurality of nucleic acid molecules that encode transcription factors. Preferably, a plurality of labels would be used in these compositions and methods.

EXAMPLES

Example 1

Monoclonal Antibodies That Specifically Bind With Human MyoD

Monoclonal antibodies having specificity for MyoD, such as the preferred antibody Mab 5.8A, have been reported in the literature (Wesche et al., Am. J. Surg. Pathol. 19:261–269 (1995); Tallini et al., Am. J. Pathol. 144:693–701 (1994); Parham et al., Acta Neuropathol. (Berl.) 87:605–611 (1994); Dias et al., Cancer Res. 52:6431–6439 (1992); Rosai et al., Am. J. Surg. Pathol. 15:974–981 (1991)). Such monoclonal antibodies can be made by a variety of methods, including the method described below Full length MyoD (such as human MyoD or hMyoD) protein is expressed in a prokaryotic expression vector using plasmids encoding a fusion protein that includes the entire amino acid sequence of MyoD protein and a tag such a FLAG. Alternatively a truncated form of MyoD is prepared by expression of a C-terminal portion of the MyoD protein and a tag such as FLAG. The vector is independently transfected into E. coli and the MyoD protein is expressed and purified. The purified full length MyoD is used as independent antigens to immunize Blab/C mice generally following established methods (see, Harrow, Antibodies, a Laboratory Manual, Cold Spring Harbor Press (1988)). Splenocytes from the immunized mice are fused with myeloma cells to produce a pool of hybridoma cells generally following established methods (Harrow, supra, (1988)). Hybridoma cells that produced anti-MyoD antibodies are identified using solid-phase immunoassays that use the purified MyoD as an immobilized antigen and clonal populations of these hybridomas are produced and maintained (see, for example, Wesche et al., Am. J. Surg. Pathol. 19:261–269 (1995); Tallini et al., Am. J. Pathol 144:693–701 (1994); Parham et al., Acta Neuropathol. (Berl.) 87:605–611 (1994); Rosai et al., Am. J. Surg. Pathol. 15:974–981 (1991)).

The monoclonal antibodies are further characterized by immunocytochemistry and western blotting using a variety of cell lines, including rhabdomyosarcoma cell lines, myogenic cell lines, small round cell tumor cell lines. Different monoclonal antibodies detectably bind with different cells, and provide a panel of monoclonal antibodies with different specificities that distinguish rhabdomyosarcoma from other small round cell tumors. Monoclonal antibodies highly specific for MyoD as determined by immunohistochemistry are identified using this method (herein designated antibody 6 and antibody 12)

Example 2

Specificity of Anti-MyoD Monoclonal Antibodies Western Blotting

Lysates of human rhabdomyosarcoma cell lines RD, Rh28 and Rh30are separated via SDS-polyacrylamide gel electrophoresis (SDS-PAGE) and are transferred to a solid support generally following established procedures (Harrow, supra, (1988)). Monoclonal antibody preparations are contacted with the solid support and the binding of the monoclonal antibody to portions of the lysates on the solid support are detected. Some of the monoclonal antibodies detectably bind with a doublet band on the solid support from each of the three cell lines. The doublet band corresponds to the molecular weight of the phosphorylated and nonphosphorylated forms of MyoD. Some of the monoclonal antibodies react with doublet bands corresponding with the molecular size of MyoD (45 kd). Some of the monoclonal antibodies give additional bands (ranging from 51 kd to 90 kd) indicating that those monoclonal antibodies react with moieties, such as proteins, other than MyoD. Some of the monoclonal antibodies may detectably bind with other members of the MyoD family, such as myogenin, myf5 and myf6 (MRF4) as determined by the molecular weight of these proteins.

Some antibody preparations, such as antibody 6 and antibody 12, are highly specific for native MyoD using extracts of a panel of small round cell tumor cell lines and western blotting of cell lysates. Monoclonal antibody 12 detectably binds with doublet bands corresponding to the molecular size of MyoD for the lysate from Rh30rhabdomyosarcoma cell line but does not detectably bind with lysates from the primitive neuroectodermal tumor cell line PFSK-1A, Burkitt's lymphoma cell line EB-2, neuroblastoma cell line SKNSH and Ewing sarcoma cell line SJSA-1.

Immunohistochemical Staining

In order to confirm that the selected monoclonal antibodies specifically bind with MyoD, the detectable binding of a monoclonal antibody to cellular structures in a variety of cells lines that express or do not express MyoD are evaluated. Cell lines that can be tested include rhabdomyosarcoma (RD, RH28, Rh30), normal human myoblasts (NHMB), mouse myoblasts (C2C12), rat myoblasts (L6), human neuroblastoma (1691, SKNSH, 1382.2, SD, 1643), human Ewing sarcoma (RD-ES, SK-ES-1, SJSA-1), human lymphoma (EB-2), human primitive neuroectodermal tumor (PFSK-1a, SK-PN-DW). Human gliblastoma multiform (U373MG) malignant schwann (NRSC).

Some monoclonal antibodies stain the nuclei of the rhabdomyosarcoma cells RD, Rh28 and Rh30. Some monoclonal antibodies stain the nuclei of primary cultures from normal human muscle (NHMB). Monoclonal antibodies that do not detectably stain the normal human myoblasts also do not detectably stain native MyoD as can be determined by western blotting. The myoblast cell line L6 does not express MyoD and can be used as control cell line.

Example 3

Diagnosis of Myosarcomas Using Monoclonal Antibodies

The methods of Example 1 and Example 2 provide monoclonal antibodies, such as antibody 12, that specifically detect MyoD in a variety of cell lines. Other monoclonal antibodies, such as Mab 5.8A (Dias et al., Cancer Res. 52:6431–6439 (1992), commercially available from Pharmagen, Dako and Neomarkers) can also be used. Monoclonal antibody 12 was evaluated for its ability to diagnose myosarcomas. Twenty samples containing small round cell neoplasms were provided by a clinical entity (Los Angeles Children's Hospital) that had diagnosed five of those twenty samples as rhabdomyosarcoma, five as primitive neuroectodermal tumors, five as Ewing's sarcoma and five as non-Hodgkin's lymphoma by visual determination. The samples were provided for testing in a blind configuration.

The samples were stained with monoclonal antibody 12. The results of the monoclonal staining conflicted with the visual diagnosis in two of the twenty samples. Table I summarizes these results. The present inventors noted that some of tumors that were diagnosed by the clinical entity as rhabdomyosarcoma detectably stained with the anti-MyoD monoclonal antibody 12. None of five lymphomas and none of the five primitive neuroectodermal tumors detectably stained with the anti-MyoD monoclonal antibody. An Ewing's sarcoma, primitive neuroectodermal tumor and Non-Hodgkins lymphoma did not detectably stain with monoclonal antibody 12 whereas the alveolar rhabdomyosarcoma sample showed strong nuclear staining with that monoclonal antibody.

TABLE I

Immunohistochemical staining of small round cell tumors for MyoD using the anti-MyoD monoclonal antibody 5.8A

|  | Anti-MyoD (antibody 12) | | Anti-Desmin | |
| --- | --- | --- | --- | --- |
|  | # Positive | Total | # Positive | Total |
| Rhabdomyosarcoma | 4* | 5 | 4 | 5 |
| Lymphoma | 0 | 5 | 0 | 5 |
| Primary neuroectodermal tumor | 0 | 5 | 0 | 5 |
| Ewing's Sarcoma | 1** | 5 | 1 | 5 |

*The one MyoD negative tumor was subsequently found to be desmin negative. It was initially diagnosed as a metastatic undifferentiated malignant tumor. Electron micrograph studies suggested a tumor with a biphenotypical differentiation. Staining with anti-MyoD and anti-desmin indicate that it is not a rhabdomyosarcoma and that it did not have a myogenic component.
**Based on histological and electron micrograph studies this tumor was diagnosed as an extra-osseus Ewing's sarcoma. Staining for MyoD and desmin results indicate that it is a rhabdomyosarcoma. Subsequence analysis by RT-PCR for EWS/any ETS was negative which greatly reduces the probability that of a diagnosis of Ewing's sarcoma or Primitive neuroectodermal tumor.

For the two samples that were diagnosed differently by visual observation by a clinical entity and by the methods of the present invention, one of the two tumors was diagnosed by the clinical entity as a rhabdomyosarcoma but did not detectably stain with monoclonal antibody 12. Subsequence analysis of this sample by staining with an anti-desmin monoclonal antibody (Dako, Carpenteria, Calif.) showed that this sample did not contain detectable amounts of desmin, which supports the diagnosis of the present invention rather than that of the clinical entity because desmin is expressed in myogenic cells. Furthermore, clinical data from the clinical entity and staining for other markers supports the diagnosis of the present invention over that of the clinical entity.

The second conflicting sample had been diagnosed by the clinical entity as a Ewing's sarcoma but stained strongly with an anti-MyoD monoclonal antibody 12. Subsequent staining with an anti-desmin antibody supported the diagnosis of rhabdomyosarcoma of the present invention. In addition, Ewing's sarcoma can be confirmed using PCR reactions because Ewings sarcomas and primitive neuroectodermal tumors are characterized by the t(11:22) chromosome translocation which leads to the juxtapositioning of a gene designated EWS on chromosome 22 with members of the ETS gene family. Ewing's sarcomas and primitive neuroectodermal tumors can be diagnosed by the presence of the EWS/ETS fusion product by reverse transcriptase-polymerase chain reaction (RT-PCR). Subsequence analysis of this sample at the clinical entity by RT-PCR for fusion products of EWS/any member of the ETS family was negative, which ruled out the diagnosis of Ewing's sarcoma or primitive neuroectodermal tumor.

Example 5

Staining of Fixed Tumor Tissues

Twenty-one paraffin-embedded tumors were stained with anti-MyoD monoclonal antibody 12. Seven of seven rhabdomyosarcoma detectably stained with that monoclonal antibody while fourteen of fourteen non-rhabdomyosarcoma tumors, including non-Hodgkins lymphomas, neuroblastomas and Ewings sarcomas did not detectably stain with that monoclonal antibody.

Example 6

Monoclonal Antibodies That Specifically Bind With Myogenin

A monoclonal antibody to myogenin (designated F5D, available from Imgenex and Pharmagen) that recognizes amino acid residues 144 to 158 of myogenin and detectably binds with human, mouse and cat myogenin by western blotting and immuno histochemical staining was used for these studies (Wright et al., Mol. Cell. Biol. 11:4104–4110 (1991); Wang et al., Am. J. Pathol. 147:1799–1810 (1995)). This monoclonal antibody was evaluated for specific binding to myogenin following the general methodologies set forth in Example 1 to Example 5 for MyoD. As shown in FIG. 1, F5D only detectably binds with the alveolar rhabdomyosarcoma cell lysate giving a single band of expected molecular size. The F5D antibody was used to distinguishing between alveolar and embryonal rhabdomyosarcoma. Two distinct patterns of staining were observed between embryonal and alveolar rhabdomyosarcoma. The embryonal rhabdomyosarcoma either did not detectably stain with antibody F5D or were sporadically stained (between about 2% and about 40% of the population of cells) with antibody F5D. In contrast, most of a population of cells (about 85% to about 95%) of the alveolar rhabdomyosarcoma were homogeneously strongly stained with antibody F5D. When staining results for tumors with antibody F5D were divided into two groups according to the level of their staining for myogenin, it was determined that sixteen of seventeen embryonal rhabdomyosarcoma did not detectably stain with antibody F5D or only a small percentage of the cells were detectably stained with antibody F5D (Table II; Table III). Alternatively, eleven of fifteen alveolar rhabdomyosarcoma strongly stained for myogenin using antibody F5D.

TABLE II

Immunohistochemical staining for myogenin in alveolar and embryonal rhabdomyosarcoma

| Group A (N, P/N, P) | | | Group B (PP, PPP) | | |
| --- | --- | --- | --- | --- | --- |
| Tumor Number | Subtype | Score | Tumor Number | Subtype | Score |
| 1 | E | N | 18 | A | PP |
| 2 | E | N | 19 | E | PP |
| 3 | E | P/N | 20 | E | PP |
| 4 | E | P/N | 21 | E | PPP |
| 5 | E | P/N | 22 | E | PPP |
| 6 | A | P/N | 23 | A | PPP |
| 7 | E | P/N | 24 | A | PPP |
| 8 | E | P/N | 25 | A | PPP |
| 9 | E | P/N | 26 | A | PPP |
| 10 | E | P/N | 27 | A | PPP |

TABLE II-continued

Immunohistochemical staining for myogenin
in alveolar and embryonal rhabdomyosarcoma

| Group A (N, P/N, P) | | | Group B (PP, PPP) | | |
|---|---|---|---|---|---|
| Tumor Number | Subtype | Score | Tumor Number | Subtype | Score |
| 11 | E | P/N | 28 | A | PPP |
| 12 | E | P/N | 29 | A | PPP |
| 13 | E | P   | 30 | A | PPP |
| 14 | E | P   | 31 | A | PPP |
| 15 | E | P   | 32 | A | PPP |
| 16 | E | P   |    |   |     |
| 17 | E | P   |    |   |     |

Key: N = Negative; P/N = occasional cells weakly positive; P = 5% cells positive; PP = 70% cells strongly positive; PPP = essentially all cells strongly positive; E = Embryonal rhabdomyosarcoma; A = Alveolar rhabdomyosarcoma. Most embryonal tumors weakly expressed myogenin whereas most alveolar tumors strongly expressed myogenin.

TABLE III

Summary of myogenin expression in rhabdomyosarcoma.

| Subtype | Group A (P, P/N, P) | Group B (PP, PPP) | Total |
|---|---|---|---|
| Embryonal | 16 | 4 | 20 |
| Alveolar | 1 | 11 | 12 |
|  |  |  | (Sum = 32) |

There was a highly significant difference in the expression of myogenin between embryonal and alveolar rhabdomyosarcoma (p = 0.0001, Fisher's exact test).

This difference in staining between embryonal and alveolar rhabdomyosarcoma was statistically significant (p=0.0001, Fisher's Exact test). These studies were performed in a blind manner without knowledge of the subtype of a tumor cell. Thus, the results of this example establish that different subclasses of tumors can be differentiated.

The distinction between subtypes of rhabdomyosarcoma (especially between alveolar and embryonal rhabdomyosarcoma) has been and continues to be a problem for surgical pathologies. Since there are clinicopathological and survival differences between the subgroups of rhabdomyosarcoma, the extensive characterization of such markers is significant. In addition, it was noted that staining for myogenin was homogeneously strong with antibody F5D for cells of alveolar rhabdomyosarcoma irrespective of cell morphology. Thus, the present invention frees pathologists from difficult morphological characterizations of tumor cells and enhances the accuracy of diagnosis with respect to treatment. In addition, it is known that there are significant differences in survival between alveolar and embryonal rhabdomyosarcoma or the other subtypes thereof, this aspect of the present invention has prognostic value and can also be used to monitor the course of a therapy and identify test compounds that be used to treat malignancies such as rhabdomyosarcoma.

Example 7

Monoclonal Antibodies That Specifically Bind With myf5

Monoclonal antibodies that specifically bind with myf5 can be made using the general methods described in Example 1 through Example 6. One method of making and identifying such monoclonal antibodies is provided below.

Antigens used as an immunogen to raise and as an antigen to screen for monoclonal antibodies that specifically bind with myf5 are derived from KLH-conjugated myf5 derived peptides and recombinant myf5 fusion proteins. KLH-conjugated human myf5 (hmyf5) is made by synthesizing a peptide that is specific for myf5, such as the sequence amino terminus-EDEDSGQLEAKHAGCH-carboxy terminus (SEQ ID NO:1) and conjugating that peptide to KLH using established procedures.

The KLH-conjugated myf5 peptide is used as an immunogen to raise splenocytes that are fused with Fo-SF-II myeloma cells to generate hybridomas generally following established methods. Supernatants from the hybridomas are initially screened for detectable binding with recombinant MyoD (myf3), myogenin (myf4), myf5 and myf6 (MRF4). Only hybridomas producing antibodies that detectably bound with myf5 but not the other members of the MyoD family are selected for further testing. Supernatants produced by the selected hybridomas are evaluated for detectable binding with unconjugated recombinant myf5 peptide (SEQ ID NO:1). Only hybridomas producing antibodies that detectably bound with recombinant myf5 protein and myf5 peptide are further evaluated. The antibodies from these selected hybridoma clones are screened using western blot analysis against cell lysates from an embryonal rhabdomyosarcoma cell lines (Rh18) that is positive for myf5 mRNA and myf5 protein by northern blot analysis and western blot analysis. Many of the selected hybridomas produced antibodies that detectably bind with the Rh18 rhabdomyosarcoma cell lysates.

Only antibodies that gave a single band of expected molecular size for myf5 are selected for further evaluation. These antibodies are further tested by western blotting and immunocytochemistry against cell lysates from a cell line transfected with a mammalian myf5 expression vector that drives the expression of exogenous myf5 in the transfected cell.

Selected anti-myf5 monoclonal antibodies are tested against a variety of small round cell tumor cell lines such as the Rh18 embryonal rhabdomyosarcoma cell line and a panel of small round cell non-myogenic tumor lines. A preferred monoclonal antibody only detectably binds with the Rh 18 cell line, preferably giving a single band of expected molecular size for myf5 and provides nuclear staining of the Rh18 embryonal rhabdomyosarcoma cells.

Example 8

Monoclonal Antibodies That Specifically Bind With myf6

The general methods used to make monoclonal antibodies that bind with myf5 in Example 7 can be used to make monoclonal antibodies that bind with myf6. Briefly, a peptide of sequence amino terminus-CPSLTGDSGPYLPSGH-carboxyl terminus (SEQ ID NO:2) that is specific for myf6 is synthesized and conjugated to KLH. Mice are immunized with the conjugated peptide generally following accepted methods to make a population of hybridomas. Supernatants from the hybridomas are screened for binding with recombinant myf3, myf4, myf5 and myf6 GST-fusion proteins, where GST was used as a negative control. Hybridomas producing antibodies that detectably bind with the recombinant myf6 are selected for further study. Western blot analysis with representative antibodies preferably only detectably bind with myf6.

These identified antibody preparations are tested for binding with cell lysates from a cell line that had been transfected with a mammalian myf6 expression vector by western blotting analysis and immunohistochemistry. The myf6 expression vector can encode the entire myf6 cDNA whose expression is under the control of a viral long terminal repeat (LTR). Only antibodies that detectably bound with the myf6-transfected cells by immunohistochemistry and by western blotting using cell lysates from the myf6-transfected cells are selected for further study.

The further selected antibodies are screened for detectable binding against a large number of small round cell tumor cell lines. Antibody preparations that detectably bind with myf6 expressing cells (giving a band of expected molecular size for myf6) are selected as potential diagnostic reagents.

All publications and documents, including patent documents, world wide web pages and scientific articles, referred to in this application are incorporated by reference in their entirety for all purposes to the same extent as if each individual publication were individually incorporated by reference.

All headings are for the convenience of the reader and should not be used to limit the meaning of the text that follows the heading, unless so specified.

BIBLIOGRAPHY

U.S. Pat. No. 3,770,383 to Price, issued Nov. 6, 1973.
U.S. Pat. No. 4,468,371 to Chen et al., issued Aug. 28, 1984.
U.S. Pat. No. 4,591,570 to Chang, issued May 27, 1986.
U.S. Pat. No. 5,223,220 to Fan et al., issued Jun. 29, 1993.
U.S. Pat. No. 5,244,788 to Hubscher, issued Sep. 14, 1993.
U.S. Pat. No. 5,270,167 to Francoeur, issued Dec. 14, 1993.
U.S. Pat. No. 5,432,099 to Ekins, issued Jul. 11, 1995.
U.S. Pat. No. 5,486,452 to Gordon et al., issued Jan. 23, 1996.
U.S. Pat. No. 5,688,918 to Kulesz-Martin, issued Nov. 18, 1997.
U.S. Pat. No. 5,763,198 to Hirth et al., issued Jun. 9, 1998.
U.S. Pat. No. 5,807,522 to Brown et al., issued Sep. 15, 1998.
U.S. Pat. No. 5,824,770 to Georgopoulos, issued Oct. 20, 1998.
U.S. Pat. No. 5,858,682 to Gruenwald et al., issued Jan. 12, 1999.
U.S. Pat. No. 5,858,801 to Brizzolara, issued Jan. 12, 1999.
U.S. Pat. No. 5,866,350 to Canavaggio et al., issued Feb. 2, 1999.
U.S. Pat. No. 5,876,949 to Dreyfuss et al., issued Mar. 2, 1999.
U.S. Pat. No. 5,885,769 to Kurnar, issued Mar. 23, 1999.
Athanasiou et al., Cell Growth Differ. 7:1525–1534 (1996).
Baringa et al., Exf. Surv. Eurkaryot. Genes 2:49–73 (1985).
Bejarano et al. Mod. Pathol. 9:445–452 (1996).
Bolon et al., Lab. Invest. 75:1–13 (1996).
Buonanno et al., Nucleic Acids Res. 20:539–544 (1992).
Dale et al., Histopatyology 14:493–502 (1989).
Dias et al., Cancer Res. 52:6431–6439 (1992).
Dias et al., Seminars in Diagnostic Pathology, 11:3–14 (1994).
DiLoreto et al, J. Clin. Pathol. 50:30–32 (1997).
Folpe et al., Mod. Pathol. 12:5–8 (1999).
Green et al., British Journal of Derrnatology 139:911–915 (1998).
Hida et al., Oral Oncol. 33:426–430 (1997).
Hirsch et al., Cancer 62:973–977 (1988).
Kishimoto et al., Cell Growth & Diff. 9:337–344 (1998).
Latchman, Transcription Factors, A Practical Approach, Second Edition, Oxford University Press, Oxford (1999).
Littlewood and Evan, Helix-Loop-Helix Transcription Factors, Third Edition, Oxford University Press, Oxford (1998).
Marcelino et al., BioTechniques, 26:11341148 (1999).
Meyyappan et al., Biol. Signals 5:130–138 (1996).
McKay et al., Am. J. Respir. Cell Mol. Biol. 18:823–833 (1998).
Maitland et al., J. Pathol. 186:275–280 (1998).
Montarras et al., The New Biologist 3:592–600 (1991).
Okuzawa et al., Electrophoresis 15:3820390 (1994).
Parham et al., Acta Neuropathol. (Berl.) 87:605–611 (1994).
Postmus et al. Cancer 57:60–63 (1986).
Rosai et al., Am. J. Surg. Pathol. 15:974–981 (1991).
Semenza, Transcription Factors in Human Disease, Oxford Monographs on Medial Genetics No. 37, Oxford University Press (1998).
Sun et al., Proc. Natl. Acad. Sci. USA 96:680–685 (1999).
Swanson, Prog. Brain Res. 92:97–113 (1992).
Tallini et al., Am. J. Pathol. 144:693–701 (1994).
Tome et al., Acta Cytol. 35:485–490 (1991).
Turner et al., Cancer Res. 58:5466–5472 (1998).
Vandromme et al., Trends Biochem. Sci. 21:59–64 (1996).
Wesche et al., Am. J. Surg. Pathol. 19:261–269 (1995).

What is claimed is:

1. A method for diagnosing clinically distinct embryonal and alveolar subtypes of rhabdomyosarcoma, comprising:
   a) contacting a reagent comprising an antibody that specifically binds myogenin with a sample that comprises at least one rhabdomyosarcoma cell or at least one extract of an rhabdomyosarcoma cell;
   b) detecting the binding of said antibody to said sample to determine the presence, absence, or amount of myogenin in said sample; and
   c) diagnosing clinically distinct embryonal and alveolar subtypes of rhabdomysarcoma, wherein alveolar rhabdomyosarcoma has an increased amount of binding as compared to embryonal rhabdomyosarcoma.

2. The method of claim 1, wherein said sample comprises at least one rhabdomyosarcoma cell.

3. The method of claim 1, wherein said sample comprises an extract of at least one rhabdomyosarcoma cell.

4. The method of claim 1, wherein said antibody is detectably labeled.

5. The method of claim 1, wherein said detecting uses a detectably labeled antibody that binds to said antibody that specifically binds to myogenin.

* * * * *

SEQUENCE LISTING

```
<160> NUMBER OF SEQ ID NOS: 2

<210> SEQ ID NO 1
<211> LENGTH: 16
<212> TYPE: PRT
<213> ORGANISM: Homo sapiens

<400> SEQUENCE: 1

Glu Asp Glu Asp Ser Gly Gln Leu Glu Ala Lys His Ala Gly Cys His
 1               5                  10                  15

<210> SEQ ID NO 2
<211> LENGTH: 16
<212> TYPE: PRT
<213> ORGANISM: Homo sapiens
```

-continued

```
<400> SEQUENCE: 2

Cys Pro Ser Leu Thr Gly Asp Ser Gly Pro Tyr Leu Pro Ser Gly His
 1               5                  10                  15
```